(12) United States Patent
Erramilli et al.

(10) Patent No.: US 12,019,655 B2
(45) Date of Patent: Jun. 25, 2024

(54) LABELING A PHARMACEUTICAL CONTENT ITEM

(71) Applicant: ACTO Technologies Inc., Toronto (CA)

(72) Inventors: Kumar Karthik Erramilli, Pickering (CA); Parth Khanna, Toronto (CA); Kapil Kalra, Mississauga (CA)

(73) Assignee: ACTO TECHNOLOGIES INC., Toronto (CA)

( * ) Notice: Subject to any disclaimer, the term of this patent is extended or adjusted under 35 U.S.C. 154(b) by 215 days.

(21) Appl. No.: 17/170,020

(22) Filed: Feb. 8, 2021

(65) Prior Publication Data

US 2022/0253460 A1 Aug. 11, 2022

(51) Int. Cl.
| | |
|---|---|
| G06F 16/00 | (2019.01) |
| G06F 16/23 | (2019.01) |
| G06F 16/28 | (2019.01) |
| G06F 16/75 | (2019.01) |
| G06F 40/289 | (2020.01) |
| G06V 20/40 | (2022.01) |
| G16H 20/13 | (2018.01) |

(52) U.S. Cl.
CPC ........ G06F 16/285 (2019.01); G06F 16/2379 (2019.01); G06F 16/75 (2019.01); G06F 40/289 (2020.01); G06V 20/49 (2022.01); G16H 20/13 (2018.01)

(58) Field of Classification Search
CPC ..... G06F 16/285; G06F 16/2379; G06F 16/75
USPC ......................................................... 707/736
See application file for complete search history.

(56) References Cited

U.S. PATENT DOCUMENTS 9,501,615 B2 * 11/2016 Eletreby ................ G16H 70/40
9,842,286 B1 * 12/2017 Miceli ................... B65C 9/0015

* cited by examiner

*Primary Examiner* — Chelcie L Daye
(74) *Attorney, Agent, or Firm* — Fernando & Partners, LLP

(57) ABSTRACT

In some implementations, a method includes obtaining a pharmaceutical content item that provides information regarding a pharmaceutical article that is associated with a plurality of pharmaceutical topics. In some implementations, the pharmaceutical content item includes a plurality of portions including a first portion and a second portion. In some implementations, the method includes determining that the first portion provides information regarding a first subset of the plurality of pharmaceutical topics and that the second portion provides information regarding a second subset of the plurality of pharmaceutical topics. In some implementations, the method includes generating a first pharmaceutical label for the first portion based on the first subset of the plurality of pharmaceutical topics and a second pharmaceutical label for the second portion based on the second subset of the plurality of pharmaceutical topics. In some implementations, the first pharmaceutical label is different from the second pharmaceutical label.

20 Claims, 18 Drawing Sheets

Create a new pharmaceutical content item 80

Name: 82
83

Competencies: 84

Behavior: 86

Include pre-labeled content: 88
89

Insert new content: 90

Figure 1F

Create a new pharmaceutical content item 82

Name: 83 84

Competencies: 86

Behavior: 88

Include pre-labeled content 90

The label you entered matches the following content: 92

2nd portion 32b

Do you want to include this existing content into the new content item that you are creating?

Yes 94a

No 94b

Insert new conten

Figure 1G

LABELING A PHARMACEUTICAL CONTENT ITEM

TECHNICAL FIELD

The present disclosure generally relates to labeling a pharmaceutical content item that provides information regarding a pharmaceutical article.

BACKGROUND

Content distribution platforms allow content creators to distribute content. Users can stream or download content via the content distribution platforms. However, some content items may include information that may not be relevant to a user.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIGS. 1A-1G are diagrams of an example operating environment in accordance with some implementations.

Figure 1A:
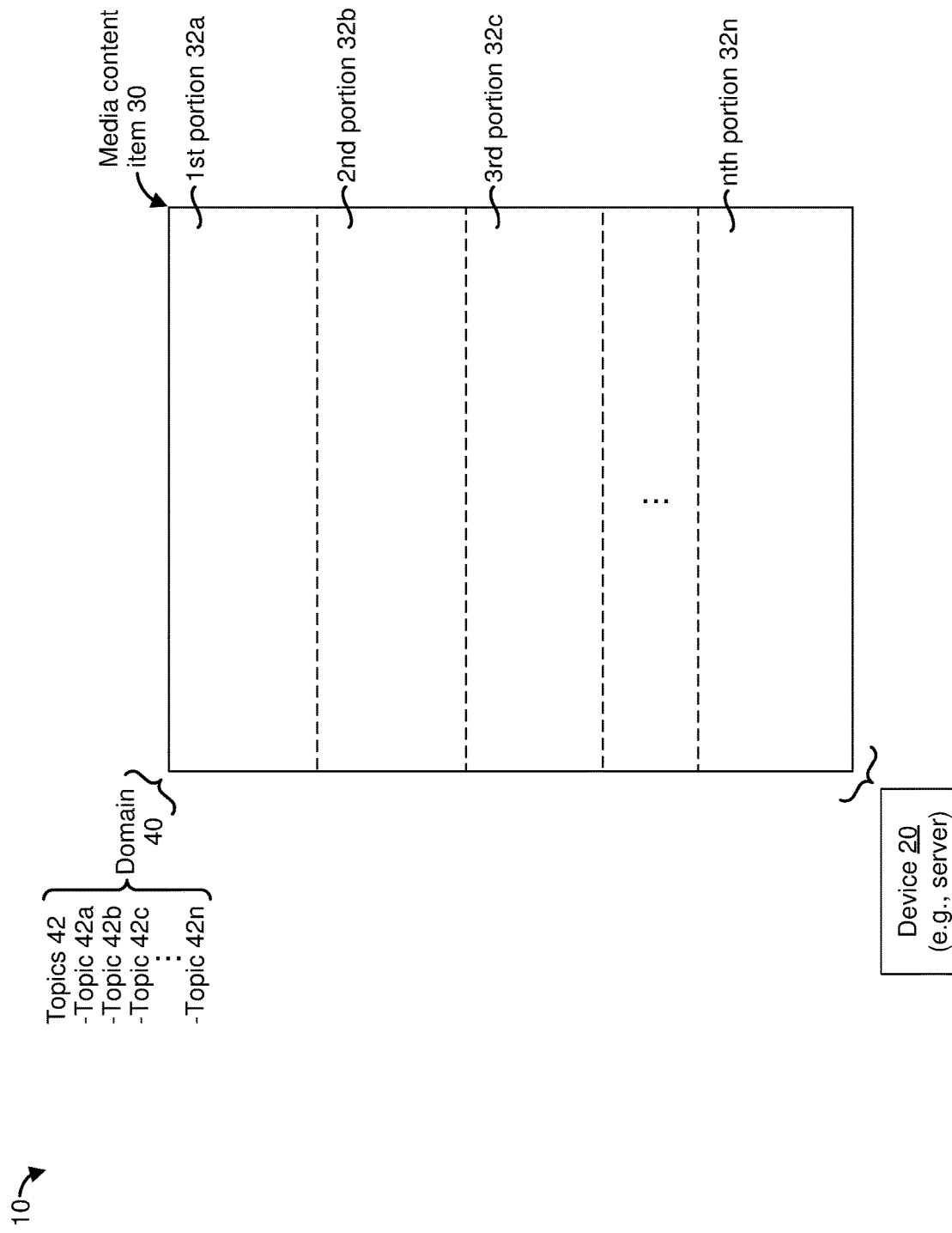

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for generating labels for different portions of a pharmaceutical content item. In various implementations, a device includes a non-transitory memory and a processor coupled with the non-transitory memory. In some implementations, a method includes obtaining a pharmaceutical content item that provides information regarding a pharmaceutical article that is associated with a plurality of pharmaceutical topics. In some implementations, the pharmaceutical content item includes a plurality of portions including a first portion and a second portion. In some implementations, the method includes determining that the first portion provides information regarding a first subset of the plurality of pharmaceutical topics and that the second portion provides information regarding a second subset of the plurality of pharmaceutical topics. In some implementations, the method includes generating a first pharmaceutical label for the first portion based on the first subset of the plurality of pharmaceutical topics and a second pharmaceutical label for the second portion based on the second subset of the plurality of pharmaceutical topics. In some implementations, the first pharmaceutical label is different from the second pharmaceutical label.

Various implementations disclosed herein include devices, systems, and methods for independently updating portions of a pharmaceutical content item. In various implementations, a device includes a non-transitory memory and a processor coupled with the non-transitory memory. In some implementations, a method includes obtaining a pharmaceutical content item that includes a plurality of portions associated with respective pharmaceutical topic labels indicative of pharmaceutical topics that the plurality of portions provides information regarding. In some implementations, the plurality of portions includes a first portion that is associated with a first pharmaceutical topic label indicative of a first pharmaceutical topic and a second portion that is associated with a second pharmaceutical topic label indicative of a second pharmaceutical topic. In some implementations, the method includes determining that the first portion satisfies an update criterion. In some implementations, the method includes utilizing the first pharmaceutical topic label to identify a pharmaceutical information source that provides information regarding the first pharmaceutical topic. In some implementations, the method includes updating the first portion based on the information provided by the pharmaceutical information source.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

Content distribution platforms allow content creators to distribute content. Users can stream or download content via the content distribution platforms. However, a content item may include information that may not be relevant to a particular type of user. Identifying information that may be relevant to a particular type of user and filtering out information that may not be relevant to that particular type of user may become resource-intensive as a size of the content item increases and/or as the types of users increase.

Some content distribution platforms request a content creator to provide a label that is associated with a media content item as a whole. In some scenarios, the label provided by the content creator may not accurately reflect the totality of the information provided by the media content item. For example, when a media content item includes information regarding various topics, the label provided by the content creator may not accurately represent the various topics that the media content item relates to.

The present disclosure provides methods, systems and/or devices for generating labels for different portions of a media content item. A device (e.g., a server) generates labels for different portions of a media content item in addition to or instead of generating a global label for the entire content item. A label for a particular portion of the media content item can more accurately represent the information provided by that particular portion. As an example, if a first portion of a media content item provides information regarding side effects of a pharmaceutical drug, the first portion is assigned a label of 'side effects'. Similarly, if a second portion of the media content item provides information regarding administering the pharmaceutical drug, the second portion is assigned a label of 'drug administration'.

The device can generate the labels based on a textual analysis of the media content item. For example, if the media content item is a document, the device can generate and associate labels with respective portions of the document based on text corresponding to the portions. If the media content item is a video item or an audio item, the device can determine a label for a portion of a media content item based on a transcript of the speech corresponding to the video item or the audio item.

The device can generate the labels based on a scene analysis of a media content item. For example, if the media content item is a video content item, the device can generate and associate labels with respective portions of the video content item based on a frame-by-frame scene analysis of the video content item. The device can identify actions that are being performed in the video and determine the labels based on the actions. As an example, if a portion of a video depicts an action that includes a healthcare provider administering a pharmaceutical drug (e.g., via a syringe or intravenous (IV) therapy), the device can associate a label of 'drug administration' with that portion of the video even though there may be no audio corresponding to that portion of the video.

The device can generate the labels for different portions of a media content item by selecting the labels from a domain-specific vocabulary (e.g., a domain-specific glossary or a domain-specific dictionary). For example, if the media content item relates to a pharmaceutical drug, the device can generate the labels by selecting terms from a glossary that includes terms related to pharmaceutical drugs (e.g., "side effects", "drug administration", "dosage", etc.)

The labels can improve searchability of the media content item. The labels allow a user to discover specific portions of the media content item which may otherwise not be discovered as readily. For example, if a user's search query matches a label for a particular portion of a media content item, that particular portion of the media content item can be presented instead of the media content item as a whole. As an example, if the search query matches a particular portion of a video, the device can play that particular portion of the video instead of playing the video from the beginning. The labels can improve navigability of the media content item by operating as bookmarks for the media content item. For example, a user can navigate to a particular portion of the media content item by selecting the label corresponding to that particular portion.

The labels can reduce an amount of computing resources associated with updating media content items. For example, the labels allow a specific portion of the media content item to be updated when that specific portion satisfies as update criterion (e.g., when newer information indicates that the specific portion is inaccurate). The labels allow other media content items to be updated more readily. For example, a first portion of a first media content item can be used to update a second portion of a second media content item when the first portion of the first media content item and the second portion of the second media content item use the same labels.

The labels allow the device to convert unstructured data into structured data that can be stored in a datastore (e.g., a relational database). For example, after different portions of a media content item have been labeled, information provided by the portions is stored into data fields that correspond to the labels. As an example, information provided by a portion of a media content item that has been labeled with 'side effects' is populated into a data field that corresponds to side effects of a pharmaceutical drug. Storing information provided by various media content items in a datastore in a structured manner allows the device to use the stored information to generate search results for a search query, provide content recommendations and/or update media content items.

The labels allow the device to present different portions of the media content item to different types of users. The media content item may include numerous portions that provide information regarding different aspects of a pharmaceutical article. Additionally or alternatively, the media content item may include numerous portions that provide information regarding the pharmaceutical article with different levels of specificity. However, not all portions may be relevant to certain types of users. For example, a first subset of the portions may not be relevant to medical representatives (e.g., because the first subset of portions may provide information with an insufficient level of specificity). Similarly, a second subset of the portions may not be relevant to patients (e.g., because the second subset of portions may provide information that patients are not expected to view, for example, details regarding clinical studies performed on the pharmaceutical article). Further, a third subset of the portions may not be relevant to healthcare providers (e.g., because the third subset of portions may provide information that healthcare providers are not expected to view, and/or the third subset of portions may provide information with an insufficient level of specificity). Since the portions are associated with respective labels, different user types can be mapped to different sets of labels in order to allow the device to present portions that are relevant to a user type while foregoing presentation of portions that may not be relevant to the user type. For example, if a medical representative has requested to view the media content item, portions of the media content item that are labeled with labels corresponding to the medical representative user type are presented and portions of the media content item that are labeled with labels that do not correspond to the medical representative user type are not presented.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes an electronic device 20 ("device 20", hereinafter for the sake of brevity). In some implementations, the device 20 includes a server. In some implementations, the device 20 represents a set of one or more computing devices (e.g., a portion of a cloud computing platform).

In various implementations, the device 20 includes a non-transitory memory ("memory", hereinafter for the sake of brevity) that stores a media content item 30. As shown in FIG. 1A, in some implementations, the media content item 30 includes various portions. For example, the media content item 30 includes a first portion 32a, a second portion 32b, a third portion 32c, . . . , and an nth portion 32n. In some implementations, the media content item 30 indicates the separation between the portions 32a, 32b, . . . , and 32n (e.g., via headings, page breaks, bookmarks, differences in formatting, etc.). Additionally or alternatively, in some implementations, the device 20 identifies the portions 32a, 32b, 32n of the media content item 30 based on a structural analysis (e.g., by analyzing a structural form of the media content item 30) and/or a semantic analysis (e.g., by analyzing a substance of the media content item) of the media content item 30.

In some implementations, the media content item 30 includes a document, and the portions 32a, 32b, . . . , and 32n represent different phrases, sentences, paragraphs, pages, or sections of the document. In some implementations, the media content item 30 includes a video content item or an audio content item, and the portions 32a, 32b, . . . , and 32n represent different time periods within the video content item or the audio content item. In some implementations, the media content item 30 has been approved by a regulatory entity. For example, in some implementations, the media content item 30 includes a document that has been approved by the Food and Drug Administration (FDA), and the document is referred to as an FDA label or an FDA-approved label. In some implementations, the media content item 30 is associated with a creation date indicating when the media content item 30 was created, an update date indicating when the media content item 30 was last updated, and/or an expiration date indicating a date until when the media content item 30 is considered to be valid by a validating entity such as the FDA. In some implementations, the portions 32a, 32b, 32c, . . . , and 32n are associated with respective creation dates, respective update dates and/or respective expiration dates. For example, the first portion 32a may be associated with a first creation date that is different from a second creation date associated with the second portion 32b. As another example, the first portion 32a may be associated with a first expiration date that is different from a second expiration date associated with the second portion 32b.

In various implementations, the media content item 30 provides information regarding a domain 40 (e.g., a subject). In some implementations, the domain 40 relates to an article (e.g., a physical article such as a pharmaceutical article, for example, a pharmaceutical drug or a medical device). For example, in some implementations, the domain 40 relates to a pharmaceutical drug that treats a cardiac condition (e.g., a cholesterol-reducing drug such as atorvastatin). In some implementations, the domain 40 relates to a pharmaceutical drug that treats an endocrinological disease or disorder (e.g., a blood glucose reducing drug such as dapagliflozin), In some implementations, the domain 40 relates to a medical device (e.g., an insulin delivery device such as an insulin pump, a pacemaker, etc.). In some implementations, the domain 40 relates to a treatment plan (e.g., a treatment plan for treating a cardiac condition, an endocrine condition, etc.).

In various implementations, the domain 40 includes various topics 42 (e.g., a first topic 42a, a second topic 42b, a third topic 42c, . . . , and an nth topic 42n). In some implementations, the topics 42 are referred to as subdomains of the domain 40. In some implementations, the domain 40 relates to a pharmaceutical drug, and the first topic 42a relates to a pharmacological composition (e.g., a chemical composition) of the pharmaceutical drug, the second topic 42b relates to medical conditions that the pharmaceutical drug can be used to treat, the third topic 42c relates to side effects of the pharmaceutical drug, a fourth topic relates to administration of the pharmaceutical drug, . . . , and the nth topic relates to dosages of the pharmaceutical drug. In some implementations, the domain 40 relates to a medical device, and the first topic 42a relates to a structural makeup of the medical device, the second topic 42b relates to medical conditions under which the medical device can be used, the third topic 42c relates to side effects or medical risks of using the medical device, the fourth topic relates to installation of the medical device . . . , and the nth topic relates to routine maintenance of the medical device.

Figure 1B:
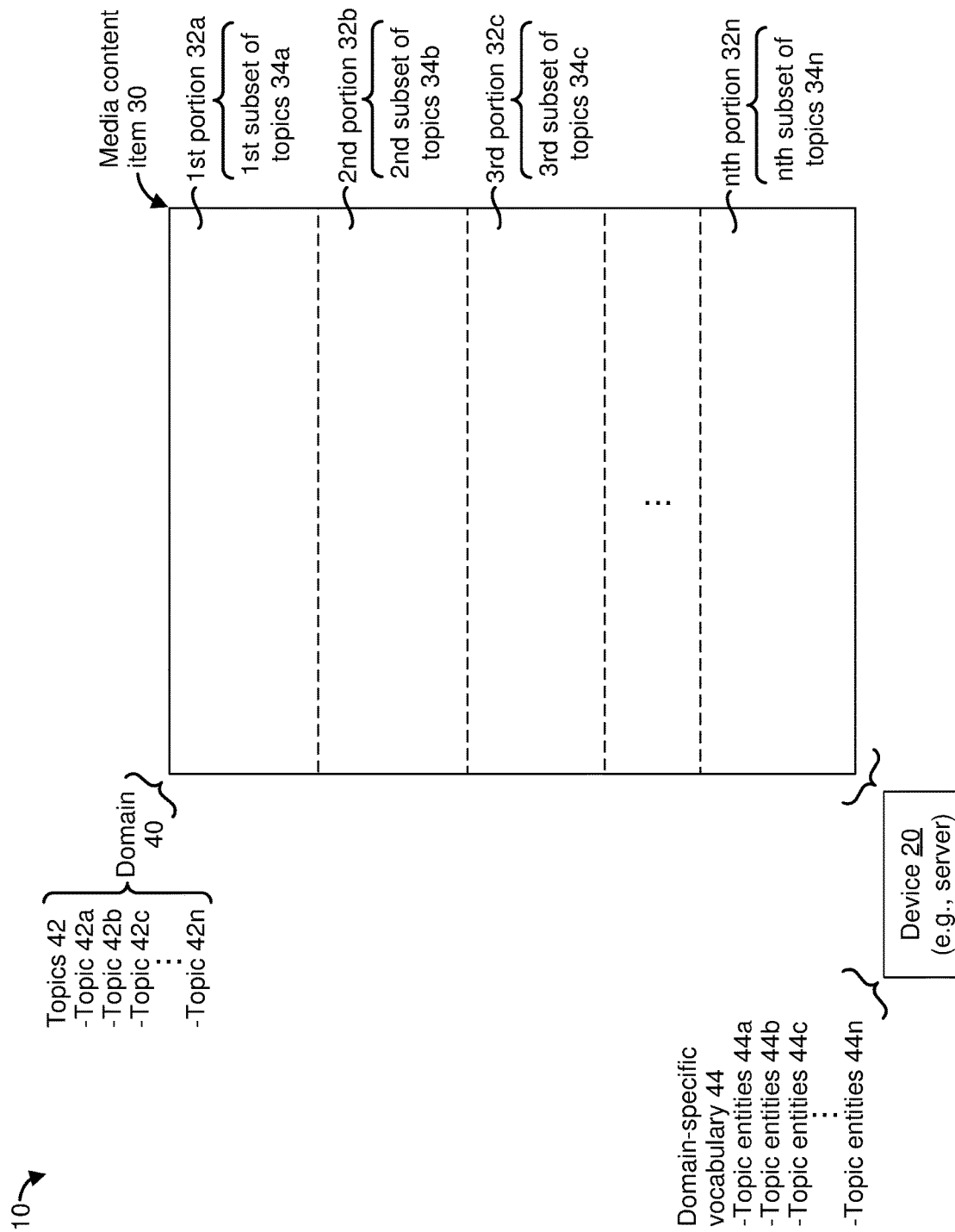

Referring to FIG. 1B, in some implementations, the device 20 determines which of the topics 42 the portions 32a, 32b, . . . , and 32n of the media content item 30 relate to. In the example of FIG. 1B, the device 20 determines that the first portion 32a provides information regarding a first subset 34a of the topics 42, the second portion 32b provides information regarding a second subset 34b of the topics 42, the third portion 32c provides information regarding a third subset 34c of the topics 42, . . . , and the nth portion 32n provides information regarding an nth subset 34n of the topics 42.

In some implementations, the device 20 utilizes a domain-specific vocabulary 44 to identify the topics that the portions 32a, 32b, . . . , and 32n relate to. In various implementations, the domain-specific vocabulary 44 includes entities that are specific to the domain 40. In some implementations, the domain-specific vocabulary 44 identifies topic-specific entities. For example, the domain-specific vocabulary 44 indicates a first set of topic entities 44a that are related to the first topic 42a, a second set of topic entities 44b that are related to the second topic 42b, a third set of topic entities 44c that are related to the third topic 42c, . . . , and an nth set of topic entities 44n that are related to the nth topic 42n. In some implementations, the topic-specific entities include terminology (e.g., a set of phrases) for a particular topic. For example, if the first topic 42a is pharmacological composition of a pharmaceutical drug, the first set of topic entities 44a includes names of compounds that are typically used to synthesize pharmaceutical drugs. As another example, if the second topic 42b is side effects of a pharmaceutical drug, the second set of topic entities 44b includes a list of side effects commonly caused by pharmaceutical drugs. In some implementations, the topic-specific entities depict actions that are related to a particular topic. For example, if the third topic 42c is administration of a pharmaceutical drug, the third set of topic entities 44c depict actions that correspond to administering a pharmaceutical drug (e.g., a first action depicting a healthcare provider injecting the pharmaceutical drug into a patient, a second action depicting a patient consuming the pharmaceutical drug orally, a third action depicting the pharmaceutical drug being infused into a patient via IV therapy, etc.).

In some implementations, the device 20 identifies which of the topics 42 the portions 32a, 32b, . . . , and 32n relate to by comparing information provided by the portions 32a, 32b, . . . , and 32n with the sets of topic entities 44a, 44b, . . . , and 44n. In some implementations, the device 20 determines that the first portion 32a is related to the first subset 34a of topics 42 in response to the first portion 32a including at least a threshold number of entities related to the first subset 34a of topics 42. For example, if the first subset 34a of topics 42 includes the second topic 42b, the device 20 determines that the first portion 32a relates to the second topic 42b in response to the first portion 32a including at least a threshold number of entities from the second set of topic entities 44b. In some implementations, the second set of topic entities 44b includes a vocabulary (e.g., a glossary) for the second topic 42b, and the device 20 determines that the first portion 32a provides information regarding the second topic 42b in response to the first portion 32a referring to at least a threshold number of phrases and/or actions from the vocabulary for the second topic 42b. For example, if the second set of topic entities 44b includes a list of side effects, the device 20 determines that the first portion 32a is related to side effects of using a pharmaceutical article in response to the first portion 132a referring to at least a threshold number of side effects.

In some implementations, the device 20 utilizes a neural network system to determine which of the topics 42 the portions 32a, 32b, . . . , and 32n relate to by providing the media content item 30 to the neural network system as an input and receiving the subsets 34a, 34b, . . . , and 34n as outputs. In some implementations, the device 20 trains the neural network system to recognize what topic a text excerpt, a video clip or an audio clip relate to during a training phase.

Figure 1C:
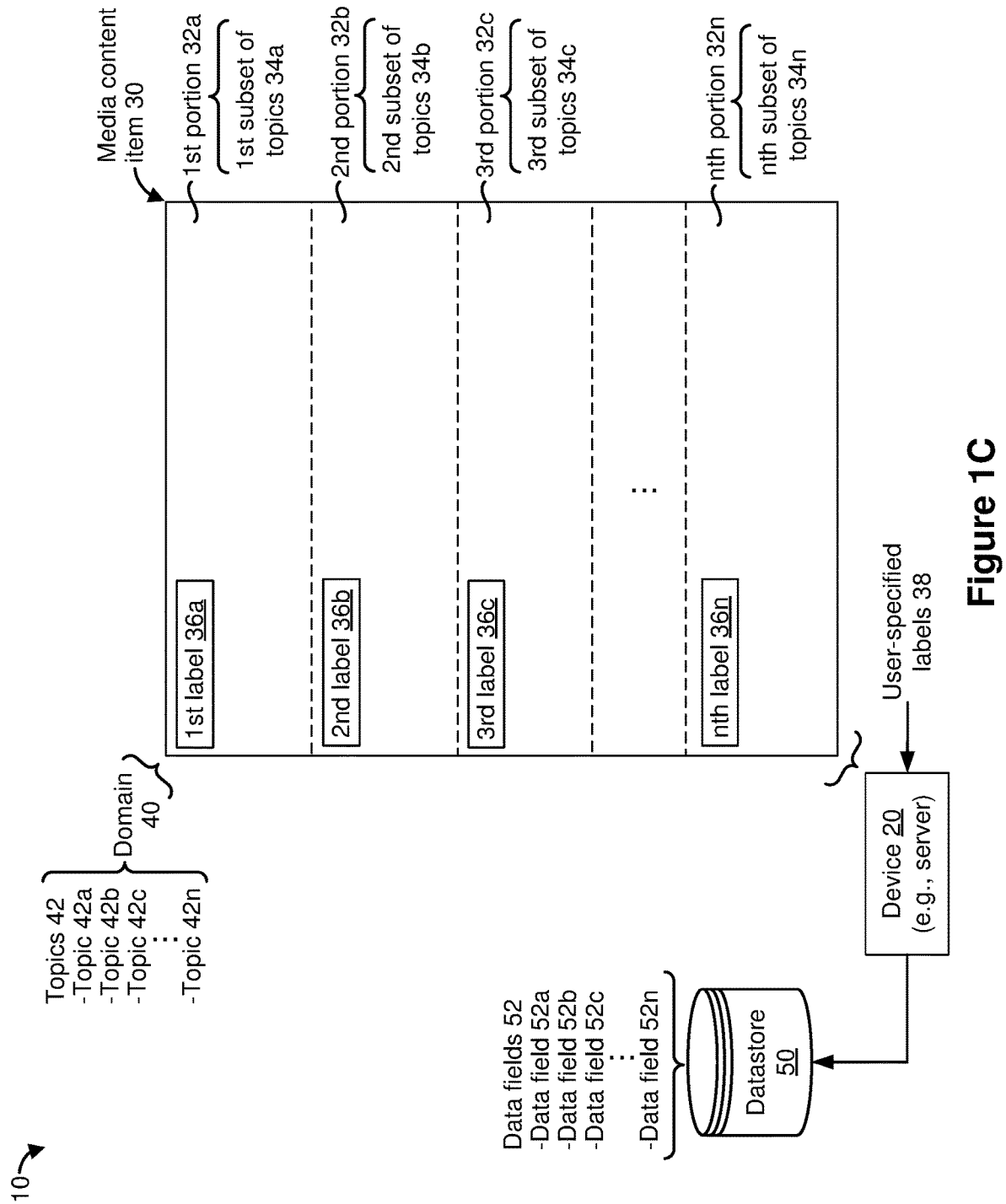

Referring to FIG. 1C, in some implementations, the device 20 generates labels for the portions 32a, 32b, . . . , and 32n based on the topics that the portions 32a, 32b, . . . , and 32n relate to. In the example of FIG. 1C, the device 20 generates a first label 36a for the first portion 32a to indicate that the first portion 32a provides information regarding the first subset 34a of topics 42, a second label 36b for the second portion 32b to indicate that the second portion 32b provides information regarding the second subset 34b of topics 42, a third label 36c for the third portion 32c to indicate that the third portion 32c provides information regarding the third subset 34c of topics 42, . . . , and an nth label 36n for the nth portion 32n to indicate that the nth portion 32n provides information regarding the nth subset of topics 42. In some implementations, the labels 36a, 36b, 36c, . . . , and 36n are collectively referred to as labels 36.

In some implementations, the labels 36a, 36b, . . . , and 36n include text. Alternatively or additionally, in some implementations, the labels 36a, 36b, . . . , and 36n include a graphic (e.g., an image). In various implementations, the labels 36a, 36b, . . . , and 36n indicate the topics that the portions 32a, 32b, . . . , and 32n relate to. For example, the first label 36a includes text and/or a graphic that indicates that the first portion 32a provides information regarding the first subset 34a of topics 42. As an example, if the first portion 32a provides information regarding a pharmacological composition of a pharmaceutical drug, the first label 36a may include the following text: 'composition', 'pharmacological composition', 'medical composition', or 'structure'. As another example, if the second portion 32b provides information regarding side effects of the pharmaceutical drug, the second label 36b may include the following text: 'side effects' or 'warnings'.

In some implementations, the device 20 generates the labels 36a, 36b, . . . , and 36n by selecting names of topics that the portions 32a, 32b, . . . , and 32n relate to. For example, if the first portion 32a provides information regarding the second topic 42b, the device 20 selects a name of the second topic 42b as the first label 36a to indicate that the first portion 32a provides information regarding the second topic 42b. More generally, in various implementations, the labels 36a, 36b, . . . , and 36n corresponds to names of topics in the corresponding subsets 34a, 34b, . . . , and 34n.

In various implementations, the device 20 generates the labels 36a, 36b, . . . , and 36n by selecting the labels 36a, 36b, . . . , and 36n from a set of predefined labels. In some implementations, the device 20 selects the labels 36a, 36b, . . . , and 36n from a set of user-specified labels 38. In some implementations, the user-specified labels 38 are provided by a content creator that created the media content item 30. For example, the content creator may provide the user-specified labels 38 to the device 20 when the content creator uploads the media content item 30 onto the device 20. Advantageously, the content creator can provide various user-specified labels 38 without having to associate the user-specified labels 38 with the appropriate portions 32a, 32b, . . . , and 32n because the device 20 performs the operation of associating the user-specified labels 38 with the appropriate portions 32a, 32b, . . . , and 32n.

In various implementations, the device 20 generates the labels 36a, 36b, . . . , and 36n in order to convert the information provided by the media content item 30 from an unstructured form into a structured form. To that end, in some implementations, the device 20 extracts information from the media content item 30, and stores the extracted information into data fields 52 of a datastore 50. In some implementations, the labels 36a, 36b, . . . , and 36n correspond to specific data fields 52 in the datastore 50. For example, the first label 36a corresponds to a first data field 52a, the second label 36b corresponds to a second data field 52b, the third label 36c corresponds to a third data field 52c, . . . , and the nth label 36n corresponds to an nth data field 52n. In some implementations, the device 20 extracts and stores information provided by the portions 32a, 32b, . . . , and 32n into the data fields 52a, 52b, and 52b that correspond to the labels 36a, 36b, . . . , and 36n associated with the portions 32a, 32b, . . . , and 32n. For example, if the first label 36a corresponds to the third data field 52c, the device 20 extracts and stores the information provided by the first portion 32a into the third data field 52c.

Figure 1D:
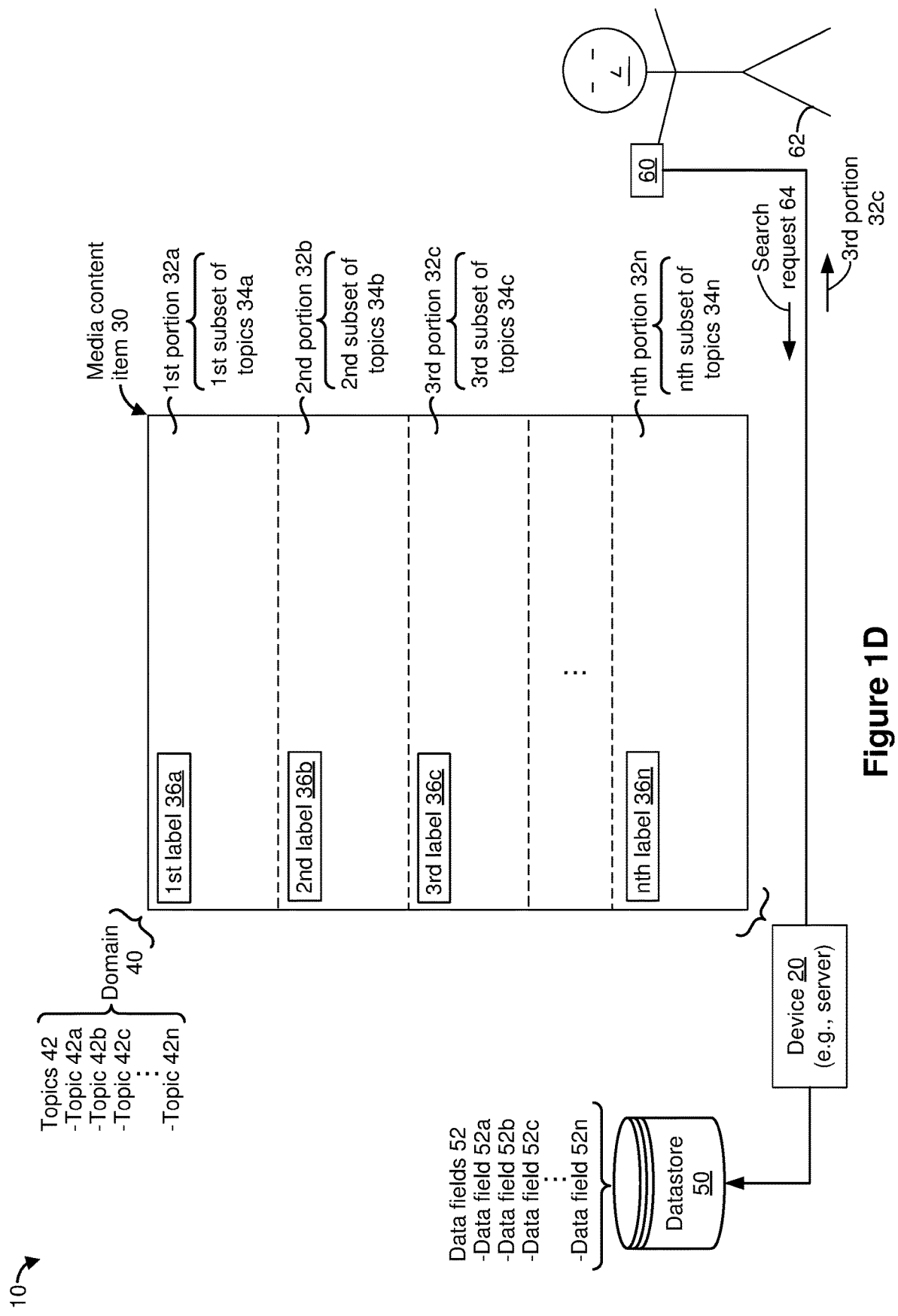

Referring to FIG. 1D, in some implementations, the operating environment 10 includes an electronic device 60 (e.g., a handheld computing device such as a smartphone, tablet, laptop, etc.) that is associated with a user 62. In some implementations, the user 62 is a medical representative (MR), and the electronic device 60 is referred to as a medical representative device (MR device). In some implementations, the user 62 is a healthcare provider (HCP), and the electronic device 60 is referred to as a healthcare provider device (HCP device). In some implementations, the user 62 is a patient, and the electronic device 60 is referred to as a patient device. In some implementations, the electronic device 60 provides a search request 64 to the device 20. The search request 64 includes a set of one or more search terms.

In the example of FIG. 1D, the device 20 interprets the search request 64 and determines that the third portion 32c of the media content item 30 is relevant to the search terms in the search request 64. As such, the device 20 provides the third portion 32c of the media content item 30 to the electronic device 60 as a search result. In some implementations, the device 20 determines that the third portion 32c is relevant to the search terms in response to the third label 36c matching the search terms in the search request 64. In some implementations, the device 20 retrieves the third portion 32c of the media content item 30 from the datastore 50. In some implementations, the device 20 determines respective relevance scores for the portions 32 of the media content item 30 based on a user type of the user 62. As such, in some implementations, different portions 32 of the media content item 30 are presented in response to the search request 64 based on the user type of the user 62. For example, while the third portion 32c may be presented in response to the search request 64 when the user 62 is a medical representative, the second portion 32b may be presented in response to the search request 64 when the user 62 is a patient.

In some implementations, the device 20 provides (e.g., transmits) the third portion 32c of the media content item 30 to the electronic device 60 and forgoes providing (e.g., transmitting) the other portions of the media content item 30 (e.g., the first portion 32a, the second portion 32b, a fourth portion, . . . , and the nth portion 32n) in order to conserve bandwidth. In some implementations, forgoing providing the other portions of the media content items 30 enhances a user experience for the user 62 by reducing a need for the user 62 to provide user inputs that correspond to manually navigating to the third portion 32c of the media content item 30. Reducing user inputs tends to enhance operability of the electronic device 60 by conserving computing resources associated with processing user inputs. As an example, if the media content item 30 is a relatively long document, the user 62 does not have to scroll through the document in order to discover and view the third portion 32c. As another example, if the media content item 30 is a relatively long video, the user 62 does not have to provide successive inputs that correspond to incrementally forwarding the video in order to discover and view the third portion 32c. As such, in various implementations, generating the labels 36a, 36b, . . . , and 36n improves discoverability of information provided by various portions of the media content item 30. In some implementations, generating the labels 36a, 36b, . . . , and 36n increases a relevance of search results by allowing the device 20 to serve specific portions of the media content item 30 instead of serving the media content item 30 in its entirety. For example, generating the labels 36a, 36b, . . . , and 36n allows the device 20 to provide the third portion 32c as a search result instead of providing the media content item 30 in its entirety as a search result.

Figure 1E:
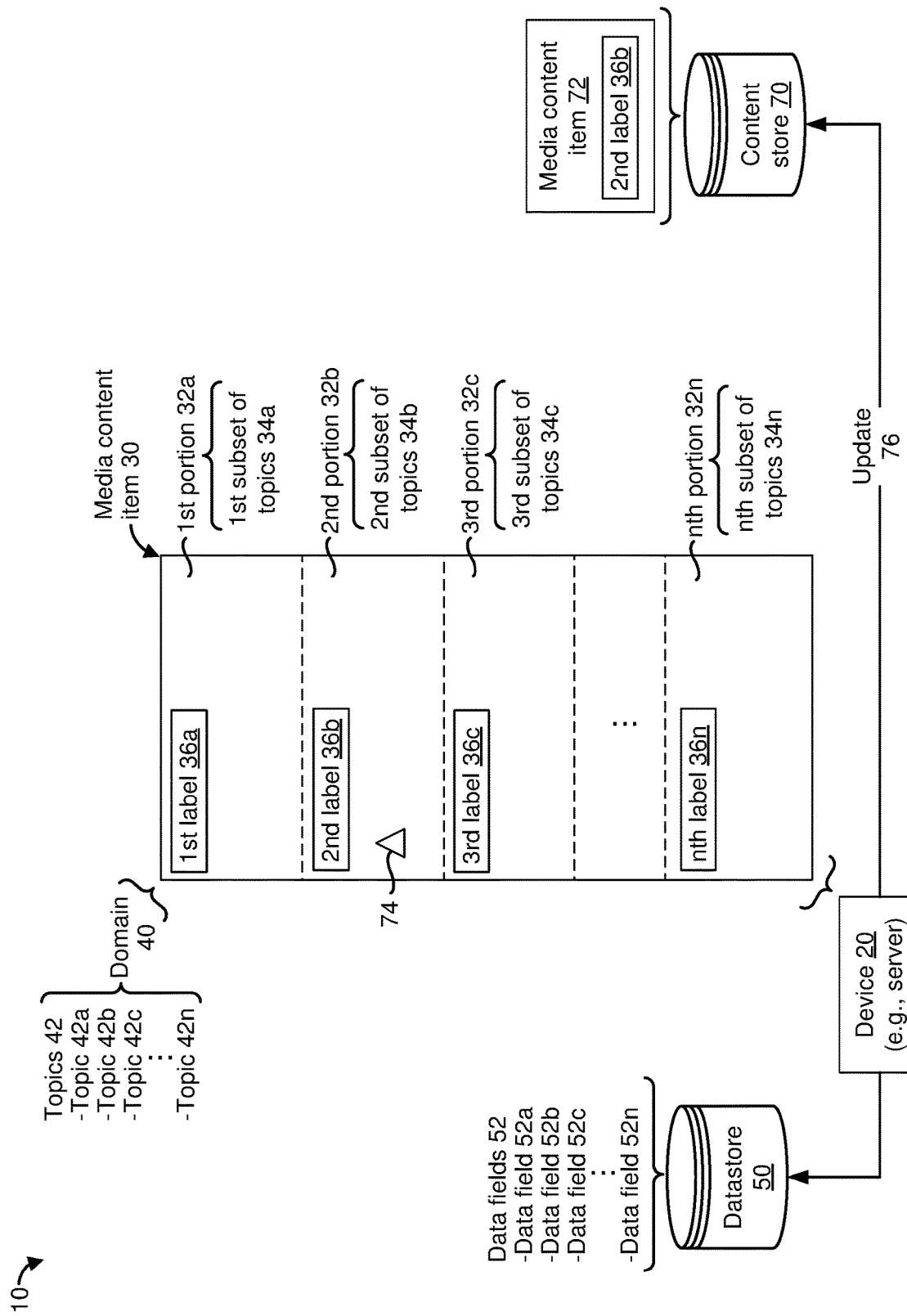

Referring to FIG. 1E, in various implementations, the device 20 utilizes the information associated with the labels 36a, 36b, . . . , and 36n to update other media content items. As shown in FIG. 1E, in some implementations, the operating environment 10 includes a content store 70 that stores various media content items such as a media content item 72. Although the content store 70 is shown as being separate from the device 20, in some implementations, the content store 70 is integrated into the device 20. In some implementations, the media content item 72 provides information that is associated with the second label 36b. For example, the media content item 72 includes information that is related to a topic that the second label 36b represents (e.g., the media content item 72 includes information that is related to the second subset 34b of topics 42). In some implementations, the media content item 72 includes at least some of the information provided by the second portion 32b of the media content item 30.

In some implementations, the device 20 detects a change 74 in the information provided by the second portion 32b of the media content item 30. For example, in some implementations, the device 20 detects that the content creator of the media content item 30 has updated the second portion 32b of the media content item 30 to remove information that is no longer relevant or accurate, and/or to add additional information (e.g., new discoveries, results of new studies). In some implementations, the device 20 generates an update 76 for the media content item 72 in response to detecting the change 74 in the second portion 32b of the media content item 30. In some implementations, the second portion 32b of the media content item 30 serves as source material for the media content item 72, and updating the media content item 72 based on changes to the second portion 32b of the media content item 30 increases a currentness (e.g., an accuracy and/or a relevance) of the media content item 72.

In various implementations, generating the labels 36a, 36b, . . . , and 36n for the media content item 30 allows the device 20 to automatically update other media content items that rely on the media content item 30 as source material thereby increasing a likelihood of downstream content staying relevant. As described in relation to FIGS. 5A-8, in some implementations, the device 20 utilizes the labels 36a, 36b, . . . , and 36n to automatically update the media content item 30.

FIG. 1F illustrates an example content generation user interface 80 for generating new pharmaceutical content items. In some implementations, the content generation user interface 80 includes a name field 82 for specifying a name 83 of a new pharmaceutical content item, a competencies field 84 for specifying competencies (e.g., skills) that the new pharmaceutical content item targets to improve, a behavior field 86 for specifying behaviors that the new pharmaceutical content item targets to enforce, a label field 88 (e.g., a tag field) that allows the inclusion of existing content by specifying a label 89 (e.g., a tag) associated with the existing content, and a content insertion field 90 for inserting new content (e.g., text, video, audio, etc.). In some implementations, the label field 88 allows a user to reference (e.g., tag) portions of media content items that have been labeled and to use a referenced portion as a template.

In some implementations, in response to detecting the label 89 being input (e.g., typed) into the label field 88, a device (e.g., the device 20 shown in FIGS. 1A-1E) determines whether the label 89 matches labels that have been associated with existing content items. For example, in some implementations, the device determines whether the label 89 entered into the label field 88 matches any of the labels 36a, 36b, . . . , and 36n shown in FIGS. 1C-1E. In some implementations, if the device determines that the label 89 matches a label that has been associated with a particular portion of an existing content item, the device provides an option to include the particular portion of the existing content item into the new pharmaceutical content item that is being created. In the example of FIG. 1G, the device determines that the label 89 entered into the label field 88 matches the second label 36b shown in FIGS. 1C-1E. As such, the device provides an option to include the second portion 32b of the media content item 30 that has been labeled with the second label 36b into the new pharmaceutical content item that is being created. In the example of FIG. 1G, the device displays a notification 92 indicating that the label 89 entered into the label field 88 matches the second label 36b assigned to the second portion 32b of the media content item 30. In some implementations, the notification 92 includes a first affordance 94a (e.g., a 'Yes' affordance) that, when selected, causes the device to include the second portion 32b of the media content item 30 into the new pharmaceutical content item that is being created. In some implementations, the notification 92 includes a second affordance 94b (e.g., a 'No' affordance) that, when selected, causes the device to not include the second portion 32b of the media content item 30 into the new pharmaceutical content item.

In some implementations, labeled portions of media content items can be used as templates for creating new media content items. For example, as described in relation to FIGS. 1F and 1G, the second portion 32b of the media content item 30 (shown in FIGS. 1C-1E) is used as a template to populate at least a portion of a new media content item. In some implementations, using labeled portions of media content items as templates expedites content creation thereby enhancing a user experience provided by the device.

In some implementations, the content generation user interface 80 recommends portions of existing media content items that can be included in the new pharmaceutical content item that is being created. In some implementations, the content generation user interface 80 detects labels in the content insertion field 90 and the content generation user interface 80 recommends portions of existing media content items that match the labels detected in the content insertion field 90.

Figure 2:
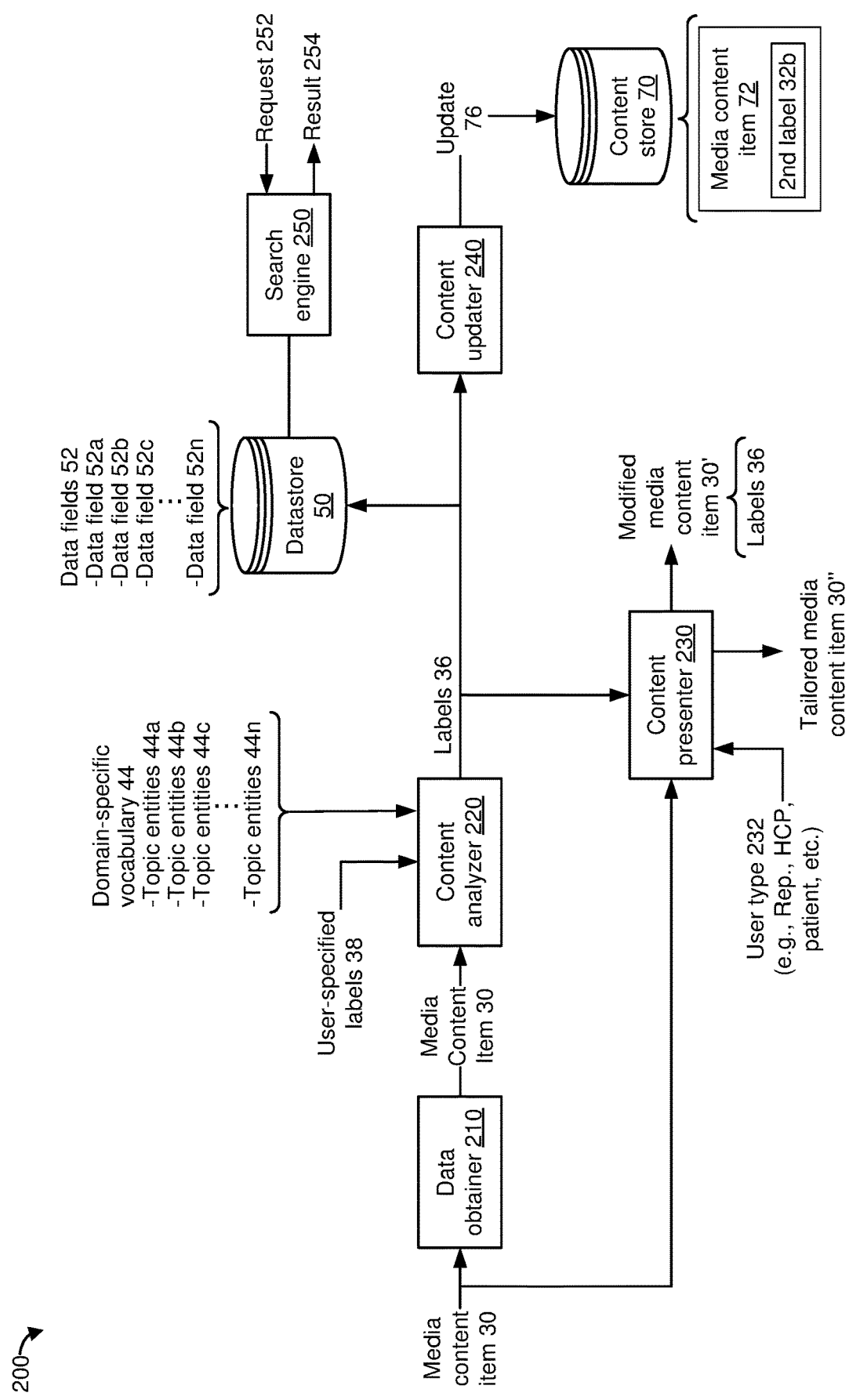
FIG. 2 is a block diagram of a content presentation engine in accordance with some implementations.

FIG. 2 illustrates a block diagram of a content presentation engine 200. In some implementations, the content presentation engine 200 resides at the device 20 shown in FIGS. 1A-1E, and performs the operations described in relation to FIGS. 1A-1G. For example, in some implementations, the device 20 shown in FIGS. 1A-1E includes the content presentation engine 200. In various implementations, the content presentation engine 200 includes a data obtainer 210 that obtains the media content item 30, and a content analyzer 220 that generates the labels 36 for different portions of the media content item 30. In some implementations, the content presentation engine 200 includes a content presenter 230 that presents a modified media content item 30' that includes the labels 36. In some implementations, the content presentation engine 200 includes a content updater 240 that utilizes the labels 36 to update the media content item 30 or other media content items that rely on the media content item 30. In some implementations, the content presentation engine 200 includes a search engine 250 that utilizes the labels 36 to provide specific portions of the media content item 30 as search results for a search query.

As shown in FIG. 2, in various implementations, the data obtainer 210 obtains the media content item 30. In some implementations, a content generation entity (e.g., a content creator) that created the media content item 30 provides (e.g., uploads) the media content item 30. In some implementations, the media content item 30 provides information regarding a pharmaceutical article (e.g., a pharmaceutical drug or a medical device), and a manufacturer of the pharmaceutical article provides the media content item 30. In some implementations, the data obtainer 210 retrieves the media content item 30 from a remote datastore. For example, in some implementations, the data obtainer 210 retrieves the media content item 30 from a datastore controlled by (e.g., a website maintained by) the manufacturer of the pharmaceutical article. In some implementations, the data obtainer 210 retrieves the media content item 30 from a datastore controlled by (e.g., a website maintained by) a regulatory entity (e.g., a regulatory agency such as the FDA). In some implementations, the data obtainer 210 provides the media content item 30 to the content analyzer 220 for analysis. In some implementations, the data obtainer 210 provides the media content item 30 to the content presenter 230 for presentation.

In various implementations, the content analyzer 220 generates the labels 36 for various portions of the media content item 30 in order to indicate topics that the various portions of the media content item 30 relate to. In some implementations, the content analyzer 220 generates the labels 36 by comparing the information provided by the media content item 30 with the domain-specific vocabulary 44. In some implementations, the content analyzer 220 determines that a particular portion of the media content item 30 relates to a particular topic in response to the particular portion including at least a threshold number of entities from a set of topic entities that correspond to that particular topic. In some such implementations, the content analyzer 220 selects a name of that particular topic as a label for that particular portion of the media content item 30. To that end, in some implementations, the content analyzer 220 accesses the domain-specific vocabulary 44 and the sets of topic entities 44a, 44b, . . . , and 44n.

In various implementations, the content analyzer 220 generates the labels 36 by selecting the labels 36 from a set of predefined labels. For example, in some implementations, the content analyzer 220 selects the labels 36 from the set of user-specified labels 38. In some implementations, the content analyzer 220 generates the labels 36 by assigning at least a subset of the user-specified labels 38 to various portions of the media content item 30 by matching the user-specific labels 38 with information provided by the various portions of the media content item 30.

In some implementations, the content analyzer 220 includes a neural network system that generates the labels 36 for various portions of the media content item 30. For example, in some implementations, the neural network system receives the media content item 30, and the domain-specific vocabulary 44 and/or the user-specified labels 38 as inputs, and generates the labels 36 as outputs. In some implementations, the neural network system is trained with a training data set that includes numerous media content items and expert-curated labels that are associated with portions of the media content items in the training data set.

In some implementations, the content analyzer 220 converts information provided by the media content item 30 from an unstructured form to a structured form by selectively storing at least portions of the information in the datastore 50. In some implementations, the content analyzer 220 extracts information that is associated with the labels 36 from the media content item 30, and stores the extracted information into data fields 52 that correspond to the labels 36. In some implementations, the content analyzer 220 provides the labels 36 to the content presenter 230.

In some implementations, the content presenter 230 modifies the media content item 30 based on the labels 36 to generate a modified media content item 30' that includes the labels 36. In some implementations, the content presenter 230 triggers presentation of the modified media content item 30' on an electronic device (e.g., on an end user's device, for example, on the electronic device 60 shown in FIG. 1D). In some implementations, the labels 36 are selectable and in response to detecting a selection of one of the labels, a portion of the modified media content item 30' that corresponds to the selected label is presented thereby improving navigability of the media content item 30 by allowing a user (e.g., the user 62 shown in FIG. 1D) to navigate through the modified media content item 30' by selecting the labels 36.

In some implementations, the content presenter 230 obtains information indicating a user type 232 of a user that has requested to view the media content item 30. Examples of the user type 232 include a medical representative that is responsible for discussing a pharmaceutical article with healthcare providers, a healthcare provider (HCP) that is responsible for treating medical conditions that the pharmaceutical article treats, and a patient. In some implementations, different user types are associated with different ones of the labels 36. In some implementations, the content presenter 230 generates a tailored media content item 30" that includes portions of the media content item 30 that are labeled with the labels 36 that are associated with the user type 232, and does not include portions of the media content item 30 that are labeled with the labels 36 that are not associated with the user type 232. As such, the tailored media content item 30" includes portions of the media content item 30 that are relevant to a user type of the user and the tailored media content item 30" does not include portions of media content item 30 that are not relevant to the user type of the user.

In some implementations, the tailored media content item 30" is presented as a set of graphical user interface (GUI) elements within a GUI of a device. In some implementations, different user types are associated with a different set of GUI elements. For example, in some implementations, the medical representatives are provided the tailored media content item 30" via a medical representative GUI that includes a coaching scenario with data fields for information included in a clinical paper, and the HCPs are provided the tailored media content item 30" via an HCP GUI that includes a data field for a clinical summary of the clinical paper. In such implementations, if the user type 232 is HCP, the content presenter 230 includes a portion of the media content item 30 that is labeled with "clinical summary" into the tailored media content item 30" for the HCP user and does not include portions of the media content item 30 that are labeled with "characteristics of control group", "phase 1 results", "phase 2 results", "phase 3 results", etc. Since the HCP user may not have time to review the clinical paper in detail, the tailored media content item 30" for the HCP user includes a clinical summary of the clinical paper and not details regarding the control group or the testing phases. However, if the user type 232 is medical representative, the content presenter 230 may include portions of the media content item 30 that are labeled with "clinical summary", "characteristics of control group" and "phase 3 results" and may not include portions of the media content item 30 labeled with "phase 1 results" and "phase 2 results". Since the medical representative user may need to know details regarding the control group and phase 3 testing in order to effectively discuss the pharmaceutical article with HCPs, the tailored media content item 30" for the medical representative user includes details regarding the control group and the phase 3 testing. As such, by generating the tailored media content item 30", the content presenter 230 presents portions of the media content item 30 that may be relevant to the user type 232 while foregoing presentation of other portions of the media content item 30 that may not be relevant to the user type 232 and may detract from a user experience.

In some implementations, the content updater 240 utilizes the labels 36 to update another media content item (e.g., the media content item 72 stored in the content store 70) that is related to at least one of the portions of the media content item 30. In some implementations, the content updater 240 uses the labels 36 to identify (e.g., search for) other media content items that provide information regarding topics represented by the labels 36. In the example of FIGS. 1E and 2, the content updater 240 has identified that the media content item 72 provides information regarding the same topic as the second portion 32b of the media content item 30 (e.g., because the media content item 72 includes the second label 36b or the information provided by the media content item 72 includes at least a threshold number of entities from a set of topic entities related to the second label 36b).

In some implementations, the content updater 240 determines whether the media content item 30 can be used to update the other media content item. In some implementations, the content updater 240 determines whether the media content item 30 includes information that is more current, relevant and/or accurate than information provided by the other media content item (e.g., the content updater 240 determines whether the media content item 30 has a greater currentness score, relevance score and/or accurateness score than the media content item 72). If the information provided by the media content item 30 is more current, relevant and/or accurate than the information provided by the other media content item, the content updater 240 generates the update 76 for the other media content item. In the example of FIGS. 1E and 2, the content updater 240 generates the update 76 in response to determining that the second portion 32b of the media content item 30 includes information that is more current, relevant and/or accurate than the media content item 72. As such, in the example of FIGS. 1E and 2, the content updater 240 updates the media content item 72 based on the information provided by the second portion 32b of the media content item 30 in order to increase a currentness, relevance and/or accuracy of the media content item 72. Advantageously, the content creator of the media content item 72 does not have to utilize computing resources to update the media content item 72 in order to maintain a currentness, relevance and/or accuracy of the media content item 72.

In various implementations, the search engine 250 receives a search request 252 and generates a search result 254 for the search request 252 based on information stored in the datastore 50. As described in relation to FIG. 1D, in some implementations, the search result 254 includes a particular portion of a media content item (e.g., the media content item 30), for example, instead of an entirety of the media content item. In some implementations, the search engine 250 generates and maintains an index of the labels 36 associated with the media content item 30, and labels associated with various other media content items. In some such implementations, the search engine 250 generates the search result 254 by ranking labels in the index based on search terms in the search request 252, and providing a portion of a media content item that is associated with the label that ranks the highest. In some implementations, the search engine 250 transmits a relevant portion of a media content item while forgoing transmission of a remainder of the media content item thereby conserving bandwidth and/or reducing resource utilization associated with navigating through the entirety of the media content item.

Figure 3:
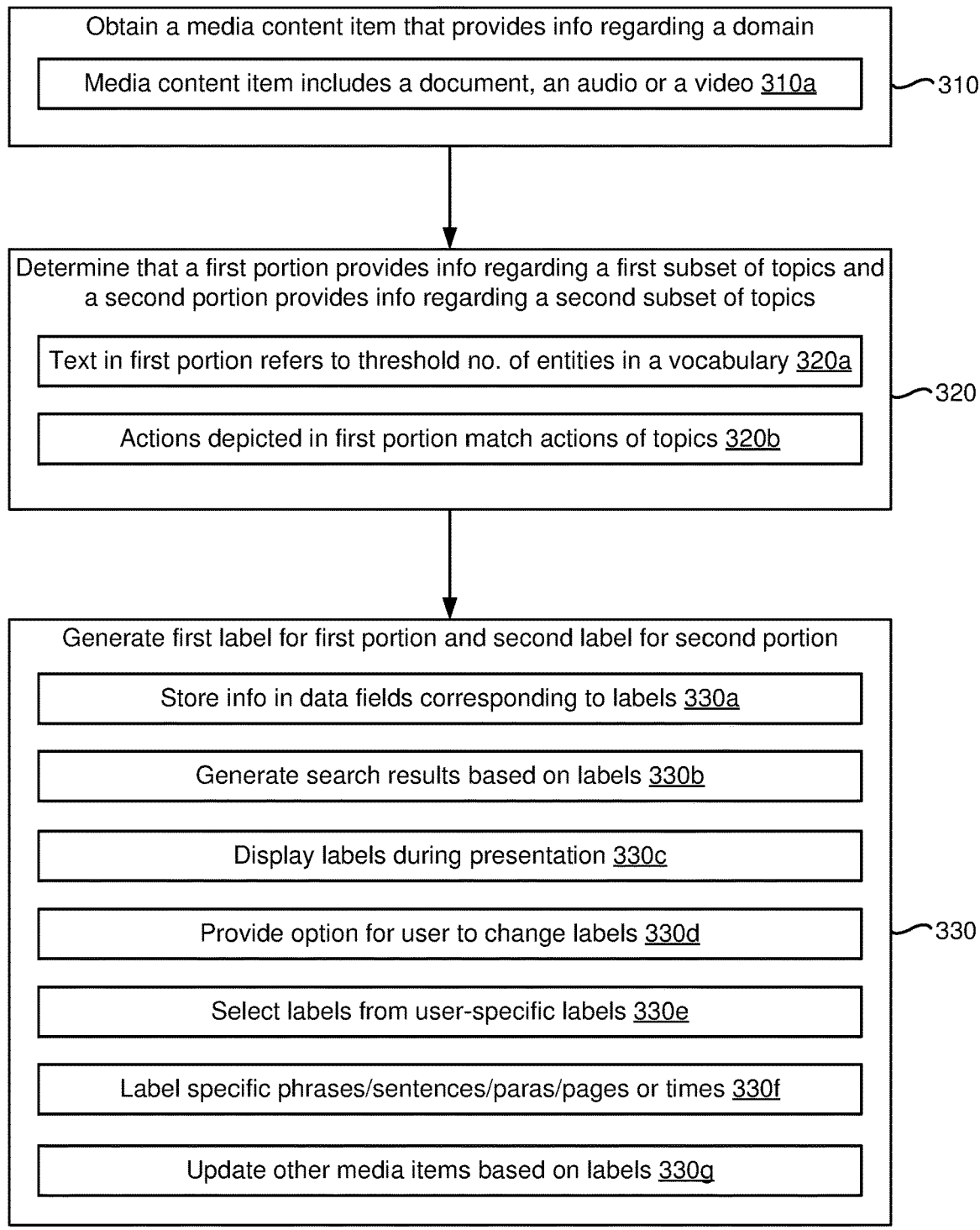
FIG. 3 is a flowchart representation of a method of generating labels for different portions of a media content item in accordance with some implementations.

FIG. 3 is a flowchart representation of a method 300 of generating pharmaceutical labels for different portions of a pharmaceutical content item. In various implementations, the method 300 is performed by a device including a non-transitory memory and a processor coupled with the non-transitory memory (e.g., the device 20 shown in FIGS. 1A-1E, and/or the content presentation engine 200 shown in FIG. 2). In some implementations, the method 300 is performed by processing logic, including hardware, firmware, software, or a combination thereof. In some implementations, the method 300 is performed by a processor executing code stored in a non-transitory computer-readable medium (e.g., a memory). In some implementations, the method 300 is performed by a server. In some implementations, the method 300 is performed at a cloud computing platform.

As represented by block 310, in various implementations, the method 300 includes obtaining a pharmaceutical content item that provides information regarding a pharmaceutical article that is associated with a plurality of pharmaceutical topics. For example, as shown in FIGS. 1A-1E, the device 20 obtains the media content item 30 that relates to the domain 40 that is associated with the topics 42. In some implementations, the pharmaceutical content item includes a plurality of portions including a first portion and a second portion. For example, as shown in FIGS. 1A-1E, the media content item 30 includes the portions 32a, 32b, . . . , and 32n. In some implementations, the pharmaceutical article includes a pharmaceutical drug or a medical device. In some implementations, the pharmaceutical topics include pharmacological composition, dosages, side effects, method of administration, etc.

As represented by block 310a, in some implementations, the pharmaceutical content item includes a document, an audio content item or a video content item. In some implementations, the pharmaceutical content item is generated (e.g., created) by a content creation entity. In some implementations, the pharmaceutical content item is created by a manufacturer of the pharmaceutical article. In some implementations, the pharmaceutical content item is validated by a content validation entity. For example, in some implementations, the pharmaceutical content item is validated by a regulatory entity such as the FDA. In some implementations, the pharmaceutical content item includes an FDA-approved drug label or an FDA-approved medical device label ("FDA label", hereinafter for the sake of brevity). In some implementations, the method 300 includes retrieving the pharmaceutical content item from a remote data source. In some implementations, the method 300 includes receiving the pharmaceutical content item from another device.

As represented by block 320, in some implementations, the method 300 includes determining that the first portion provides information regarding a first subset of the plurality of pharmaceutical topics and that the second portion provides information regarding a second subset of the plurality of pharmaceutical topics. For example, as shown in FIG. 1B, the device 20 determines that the first portion 32a provides information regarding the first subset 34a of the topics 42, the second portion 32b provides information regarding the second subset 34b of the topics 42, . . . , and the nth portion 32n provides information regarding the nth subset 34n of the topics 42.

As represented by block 320a, in some implementations, determining that the first portion provides information regarding the first subset of the plurality of pharmaceutical topics includes determining that text in the first portion includes more than a threshold number of phrases that refer to entities in a vocabulary associated with the first subset of the plurality of pharmaceutical topics. For example, as described in relation to FIG. 1B, the device 20 compares text of the portions 32a, 32b, . . . , and 32n with entities included in the domain-specific vocabulary 44 to determine the topics that the portions 32a, 32b, . . . , and 32n relate to. As an example, if a particular portion of a document uses phrases that are used when discussing administration of a pharmaceutical drug (e.g., "inject", "infuse", "eat", "drink", etc.), the device determines that the particular portion relates to administration of a pharmaceutical drug. In some implementations, the first portion includes a video or an audio, and the method 300 further includes generating the text by performing a speech-to-text operation on the video or the audio in the first portion.

As represented by block 320b, in some implementations, the first portion includes a video, and determining that the first portion provides information regarding the first subset of the plurality of pharmaceutical topics includes performing instance segmentation on the video in order to identify a set of one or more objects represented in the video, In some implementations, the objects include persons and/or medical equipment such as syringes, etc. In some implementations, the method 300 further includes performing semantic segmentation on the video to identify a set of actions that the set of one or more objects are performing in the video (e.g., recognizing that a first person is using a syringe to inject a fluid into a second person). In some implementations, the method 300 further includes determining that the set of actions being performed in the video are within a similarity threshold of actions that are associated with the first subset of the plurality of topics. For example, determining that an action depicting the first person using the syringe to inject the second person with fluid is within a similarity threshold of an action corresponding to a healthcare provider injecting a patient with a pharmaceutical drug. As described in FIG. 1B, in some implementations, the sets of topic entities 44a, 44b, . . . , and 44n specify actions that are specific to their corresponding topics, and the device 20 identifies the topics of the portions 32a, 32b, . . . , and 32n by matching actions depicted in the portions 32a, 32b, 32n with actions specified in the sets of topic entities 44a, 44b, . . . , and 44n.

As represented by block 330, in some implementations, the method 300 includes generating a first pharmaceutical label for the first portion based on the first subset of the plurality of pharmaceutical topics and a second pharmaceutical label for the second portion based on the second subset of the plurality of pharmaceutical topics. In some implementations, the first pharmaceutical label is different from the second pharmaceutical label. For example, as shown in FIG. 1C, the device 20 generates the first label 36a for the first portion 32a to indicate that the first portion 32a provides information regarding the first subset 34a of the topics 42, and the second label 36b for the second portion 32b to indicate that the second portion 32b provides information regarding the second subset 34b of the topics 42.

As described herein, in some implementations, generating the labels improves discoverability of the various portions of the media content item. For example, in some implementations, a user can navigate to a specific portion of the media content item by selecting a label that corresponds to that specific portion of the media content item. Selecting the label reduces a need for user inputs that correspond to incrementally navigating through the media content item in order to view a desired portion of the media content item. In some implementations, reducing the need for user inputs tends to enhance operability of the device by reducing utilization of computing resources and power consumption associated with processing (e.g., detecting, interpreting and/or acting upon) user inputs. In some implementations, reducing the need for user inputs tends to enhance a user experience of the user.

As described herein, in some implementations, generating the labels tends to increase a relevance of a search result provided by the device in response to receiving a search request. For example, in some implementations, the device determines that search terms in the search request match a label associated with a particular portion of the media content item, and the device provides that particular portion of the media content item as a search result while forgoing providing other portions of the media content item. Providing a portion of the media content item that matches the search request while forgoing providing other portions improves a relevance of the search results. In some implementations, transmitting a portion of the media content item that is relevant to the search request while forgoing transmission of other portions of the media content item that are not relevant to the search request conserves bandwidth.

As represented by block 330a, in some implementations, the method 300 further includes storing the information provided by the first portion in association with a first data field that corresponds to the first pharmaceutical label, and storing the information provided by the second portion in association with a second data field that corresponds to the second pharmaceutical label. For example, as described in relation to FIGS. 1C and 2, the device 20 and/or the content presentation engine 200 extracts and stores information associated with the labels 36 into data fields 52 that correspond to the labels 36. In some implementations, the method 300 includes generating an index (e.g., a mapping) that maps labels to the specific portions of the media content items that the labels are associated with. In various implementations, storing the information associated with the first and second labels into corresponding data fields increases a likelihood of the first and second portions of the media content item being searchable. For example, storing the information provided by the first and second portions into an indexed datastore increases a likelihood of the information being served as part of search results for search requests.

As represented by block 330b, in some implementations, the method 300 further includes obtaining a search request that includes a set of one or more search terms. In some implementations, the method 300 includes in accordance with a determination that the set of one or more search terms matches the first pharmaceutical label, presenting the first portion of the pharmaceutical content item and forgoing presentation of other portions of the pharmaceutical content item. In some implementations, the method 300 includes in accordance with a determination that the set of one or more search terms matches the second pharmaceutical label, presenting the second portion of the pharmaceutical content item and forgoing presentation of other portions of the pharmaceutical content item. For example, as discussed in relation to FIG. 1D, the device 20 transmits the third portion 32c of the media content item 30 to the electronic device 20 as a search result while forgoing transmission of the remaining portions of the media content item 30 in response to determining that search terms in the search request 64 match the third label 36c. In various implementations, the device increases a relevance of search results by presenting a particular portion of a media content item even when that particular portion of the media content item is not positioned at a beginning of the media content item.

In some implementations, the method 300 includes obtaining a search request that includes a set of one or more search terms. In some implementations, the method 300 includes, in accordance with a determination that the set of one or more search terms match the first pharmaceutical label, playing the video from the first time to the second time and forgoing playback of the video from the third time to the fourth time. In some implementations, the method 300 includes, in accordance with a determination that the set of one or more search terms match the second pharmaceutical label, playing the video from the third time to the fourth time and foregoing playback of the video from the first time to the second time. In some implementations, playing a portion of the video that is relevant to the search request reduces a need for user inputs corresponding to scrubbing through (e.g., incrementally fast-forwarding) the video to navigate to the relevant portion of the video. Reducing the need for user inputs tends to extend a battery-life of a battery-operated device. In some implementations, forgoing playback of a portion of the video that is not relevant to the search request enhances operability of the device by conserving power associated with playing content.

As represented by block 330c, in some implementations, the method 300 includes displaying the first pharmaceutical label and foregoing display of the second pharmaceutical label while the first portion of the pharmaceutical content item is being presented, and displaying the second pharmaceutical label and foregoing display of the first pharmaceutical label while the second portion of the pharmaceutical content item is being presented. For example, as discussed in relation to FIG. 2, in some implementations, the content presenter 230 modifies the media content item 30 to generate a modified media content item 30' that includes the labels 36, and the labels 36 are selectively displayed when corresponding portions of the modified media content item 30' are being presented. In some implementations, the labels indicate the topics that the first and second portions relate to thereby reducing a need for user inputs that correspond to scrubbing through (e.g., incrementally fast-forwarding or rewinding) the first and second portions in order to discern what the first and second portions relate to.

As represented by block 330d, in some implementations, the method 300 includes detecting a user input corresponding to a request to change the first pharmaceutical label to a third pharmaceutical label, and in response to detecting the user input, changing the first pharmaceutical label to the third pharmaceutical label while maintaining the second pharmaceutical label. In some implementations, the method 300 includes providing an option to change the labels immediately after the labels have been generated. Additionally or alternatively, in some implementations, the method 300 includes providing the option to change the labels while the media content item is being presented.

As represented by block 330e, in some implementations, generating the first pharmaceutical label comprises selecting the first pharmaceutical label from a plurality of pharmaceutical labels specified by a user. For example, as discussed in relation to FIGS. 1C and 2, in some implementations, the device 20 and/or the content presentation engine 200 generate the labels 36 by selecting a subset of the user-specified labels 38. In some implementations, obtaining the pharmaceutical content item includes detecting a user input corresponding to a request to upload the pharmaceutical content item and to associate the pharmaceutical content item with the plurality of pharmaceutical labels. Advantageously, in some implementations, the user does not have to associate labels with different portions of the media content item. The user can provide a set of labels and the device associates different portions of the media content item with appropriate labels.

As represented by block 330f, in some implementations, the pharmaceutical content item includes a plurality of pages. In such implementations, the first pharmaceutical label is associated with a first subset of the plurality of pages, and the second pharmaceutical label is associated with a second subset of the plurality of pages that is different from the first subset of the plurality of pages. For example, in some implementations, each of the portions 32a, 32b, . . . , and 32n shown in FIGS. 1A-1E includes a set of one or more pages.

In some implementations, the pharmaceutical content item includes a plurality of paragraphs. In such implementations, the first pharmaceutical label is associated with a first subset of the plurality of paragraphs, and the second pharmaceutical label is associated with a second subset of the plurality of paragraphs that is different from the first subset of the plurality of paragraphs. For example, in some implementations, each of the portions 32a, 32b, . . . , and 32n shown in FIGS. 1A-1E includes a set of one or more paragraphs. In some implementations, the labels are associated with different sentences (e.g., the first label is associated with a first sentence and the second label is associated with a second sentence that is different from the first sentence). For example, in some implementations, each of the portions 32a, 32b, . . . , and 32n shown in FIGS. 1A-1E includes a set of one or more sentences. In some implementations, the labels are associated with different phrases (e.g., the first label is associated with a first phrase and the second label is associated with a second phrase that is different from the first phrase). For example, in some implementations, each of the portions 32a, 32b, . . . , and 32n shown in FIGS. 1A-1E includes a set of one or more phrases.

In some implementations, the pharmaceutical content item includes a video that spans a duration of time. In such implementations, the first pharmaceutical label is associated with a first portion of the video that starts at a first time and ends at a second time, and the second pharmaceutical label is associated with a second portion of the video that starts at a third time that is different from the first time and ends at a fourth time that is different from the second time. For example, in some implementations, each of the portions 32a, 32b, . . . , and 32n shown in FIGS. 1A-1E includes different time periods of a video.

As represented by block 330g, in some implementations, the method 300 includes updating, based on the first portion, a second pharmaceutical content item that provides information regarding the first subset of the plurality of pharmaceutical topics, and updating, based on the second portion, a third pharmaceutical content item that provides information regarding the second subset of the plurality of pharmaceutical topics. For example, as shown in FIGS. 1E and 2, in some implementations, the device 20 and/or the content presentation engine 200 (e.g., the content updater 240) updates the media content item 72 based on the information provided by the second portion 32b of the media content item 30.

In some implementations, updating the second pharmaceutical content item includes detecting that the second pharmaceutical content item includes information provided by the first portion, detecting a change in the information provided by the first portion, and updating the second pharmaceutical content item in response to detecting the change in the information provided by the first portion. For example, as discussed in relation to FIG. 1E, in some implementations, the device 20 updates the media content item 72 in response to detecting the change 74 in the second portion 32b of the media content item 30.

In some implementations, updating the second pharmaceutical content item includes detecting that the second pharmaceutical content item refers to information provided by the first portion, detecting that a validity date associated with the first portion occurs before a current date, and annotating the second pharmaceutical content item to indicate that the information extracted from the first portion is invalid. For example, in some implementations, if the second pharmaceutical content item includes information from an FDA label that is valid until a particular date, after that particular date, the device annotates the second pharmaceutical content item to indicate that the information extracted from the FDA label may no longer be valid. Advantageously, as information provided by source material becomes invalid, downstream media content items that include information from the source material are annotated to indicate that the information integrated from the source material may no longer be valid.

In some implementations, the method 300 includes obtaining a request to view the pharmaceutical content item. In some implementations, the request indicates a user type (e.g., the user type 232 shown in FIG. 2) of a user that generated the request. In some implementations, the method 300 includes, in response to the user type being a first user type that is associated with the first pharmaceutical label and not the second pharmaceutical label, displaying the first portion of the pharmaceutical content item while forgoing display of the second portion of the pharmaceutical content item. For example, as described in relation to FIG. 2, if the user type 232 is an HCP, the content presenter 230 generates the tailored media content item 30" such that the tailored media content item 30" includes portions of the media content item 30' that are labeled with a subset of the labels 36 that is associated with the HCP user type and the tailored media content item 30" does not include portions of the media content item 30' that are labeled with a remainder of the labels 36 that are not associated with the HCP user type. In some implementations, the method 300 includes, in response to the user type being a second user type that is associated with the second pharmaceutical label and not the first pharmaceutical label, displaying the second portion of the pharmaceutical content item while forgoing display of the first portion of the pharmaceutical content item. For example, as described in relation to FIG. 2, if the user type 232 is a medical representative, the content presenter 230 generates the tailored media content item 30" such that the tailored media content item 30" includes portions of the media content item 30' that are labeled with a subset of the labels 36 that is associated with the medical representative user type and the tailored media content item 30" does not include portions of the media content item 30' that are labeled with a remainder of the labels 36 that are not associated with the medical representative user type.

In some implementations, the method 300 includes detecting that a new pharmaceutical content item that is being created references the first pharmaceutical label. For example, as shown in FIGS. 1F and 1G, the device detects that the label 89 entered in the label field 88 matches the second label 36b shown in FIGS. 1C-1E. In some implementations, the method 300 includes, in response to detecting that the new pharmaceutical content item that is being created references the first pharmaceutical label, displaying an affordance that, when selected, triggers the device to include the first portion of the pharmaceutical content item into the new pharmaceutical content item. For example, as shown in FIG. 1G, the device displays the notification 92 with the first affordance 94a that, when selected, causes the device to include the second portion 32b of the media content item 30 into the new pharmaceutical content item that is being created. In some implementations, the method 300 includes, in response to detecting a user selection of the affordance, including the first portion of the pharmaceutical content item into the new pharmaceutical content item that is being created. For example, as discussed in relation to FIG. 1G, in response to a user selection of the first affordance 94a the device includes the second portion 32b of the media content item 30 into the new pharmaceutical content item that is being created.

Figure 4:
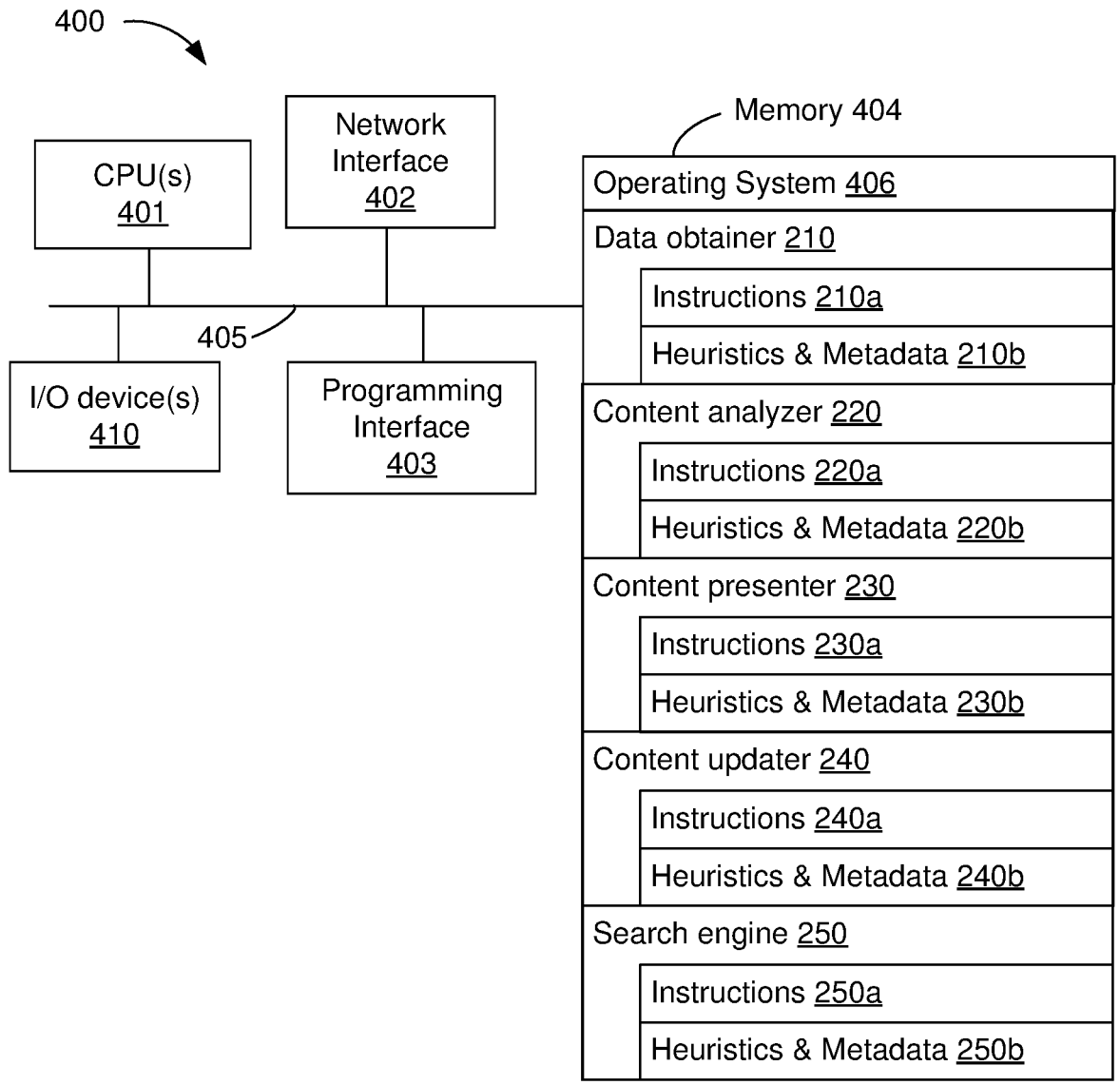
FIG. 4 is a block diagram of a device that labels different portions of a media content item in accordance with some implementations.

FIG. 4 is a block diagram of a device 400 that labels different portions of a media content item in accordance with some implementations. In some implementations, the device 400 implements the device 20 shown in FIGS. 1A-1E, and/or the content presentation engine 200 shown in FIG. 2. In some implementations, the device 400 is implemented by a server. In some implementations, the device 400 is implemented by a cloud computing platform. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the data obtainer 210, the content analyzer 220, the content presenter 230, the content updater 240, and the search engine 250. In various implementations, the device 400 performs the method 300 shown in FIG. 3.

As described herein, in various implementations, the data obtainer 210 obtains (e.g., retrieves or receives) a media content item (e.g., the media content item 30 shown in FIGS. 1A-2). To that end, the data obtainer 210 includes instructions 210a, and heuristics and metadata 210b.

As described herein, in various implementations, the content analyzer 220 determines labels (e.g., the labels 36 shown in FIG. 2) for various portions of the media content item. To that end, the content analyzer 220 includes instructions 220a, and heuristics and metadata 220b.

As described herein, in various implementations, the content presenter 230 presents portions of the media content item (e.g., the third portion 32c shown in FIG. 1D) and/or a modified version of the media content item (e.g., the modified media content item 30' and/or the tailored media content item 30" shown in FIG. 2) based on the labels determined by the content analyzer 220. To that end, the content presenter 230 includes instructions 230a, and heuristics and metadata 230b.

As described herein, in various implementations, the content updater 240 utilizes the labels to update the media content item and/or other media content items (e.g., to generate the update 76 shown in FIGS. 1E and 2). To that end, the content updater 240 includes instructions 240a, and heuristics and metadata 240b.

As described herein, in various implementations, the search engine 250 utilizes the labels to generate search results (e.g., to generate the search results 254 shown in FIG. 2). To that end, the search engine 250 includes instructions 250a, and heuristics and metadata 250b.

In various implementations, the one or more I/O devices 410 include one or more sensors. In some implementations, the one or more I/O devices 410 include an audio sensor (e.g., a microphone) for receiving an audible signal (e.g., an audible signal that corresponds to the search request 252 shown in FIG. 2). In some implementations, the one or more I/O devices 410 include a display for displaying information (e.g., for displaying the modified media content item 30' shown in FIG. 2 and/or for displaying the search results 254 shown in FIG. 2). In some implementations, the one or more I/O devices 410 include a speaker for outputting an audible signal (e.g., an audible signal that corresponds to the search results 254 shown in FIG. 2).

A media content item generated by a content generation entity (e.g., a content creator) may over time become inaccurate or irrelevant. For example, if a media content item lists side effects of a pharmaceutical drug, the list of side effects may be considered incomplete as additional side effects are discovered. As such, there may be a need to update the media content item in order to maintain an accuracy, a reliability and/or a relevance of the media content item. However, updating a media content item can be a resource-intensive operation. For example, removing outdated information from a media content item and/or adding new information to the media content item can be time-consuming.

The present disclosure provides methods, systems and/or devices for automatically updating an existing media content item based on other media content items that relate to the same topic. A device can associate topic labels with different portions of a media content item, and selectively update a particular portion of the media content item when new information becomes available regarding the topic associated with that particular portion. As an example, as described in relation to FIGS. 1A-4, if a media content item relates to a pharmaceutical drug, the device can label a first portion of the media content item that provides information regarding a formulation of the pharmaceutical drug with the label 'medical formulation', a second portion that provides information regarding uses of the pharmaceutical drug with the label 'medical uses', a third portion that provides information regarding side effects of the pharmaceutical drug with the label 'side effects', etc. In this example, when the device detects another media content item that identifies additional side effects of the pharmaceutical drug, the device can update the third portion of the media content item labeled 'side effects' to include the additional side effects.

The content generation entity can apply the labels while generating the media content item. Additionally or alternatively, the device can apply labels to an existing media content item and monitor a corpus of information associated with the labels to determine whether to update portions of the media content item. Labelling various portions of the media content item allows the device to use the labels to identify external information (e.g., information outside the bounds of the media content item) that can be used to update the various portions of the media content item. For example, labeling the third portion of the media content item with the label 'side effects' allows the device to compare the information provided by the third portion with information stored in a datastore's data field corresponding to side effects, and update the third portion using the information stored in the data field. As another example, labeling the third portion of the media content item with the label 'side effects' allows the device to update the third portion using information provided by other media content items that provide information regarding side effects of the pharmaceutical drug.

Prior to updating the media content item, the device can send a notification to the content generation entity with the proposed update, and perform the update to the media content item after receiving an approval message from the content generation entity. Requesting the content generation entity to approve proposed updates to the media content item ensures that the content generation entity maintains control of the information provided by the media content item. The updated portion of the media content item can indicate that the update was approved by the content generation entity thereby maintaining an authenticity of the media content item.

Figure 5A:
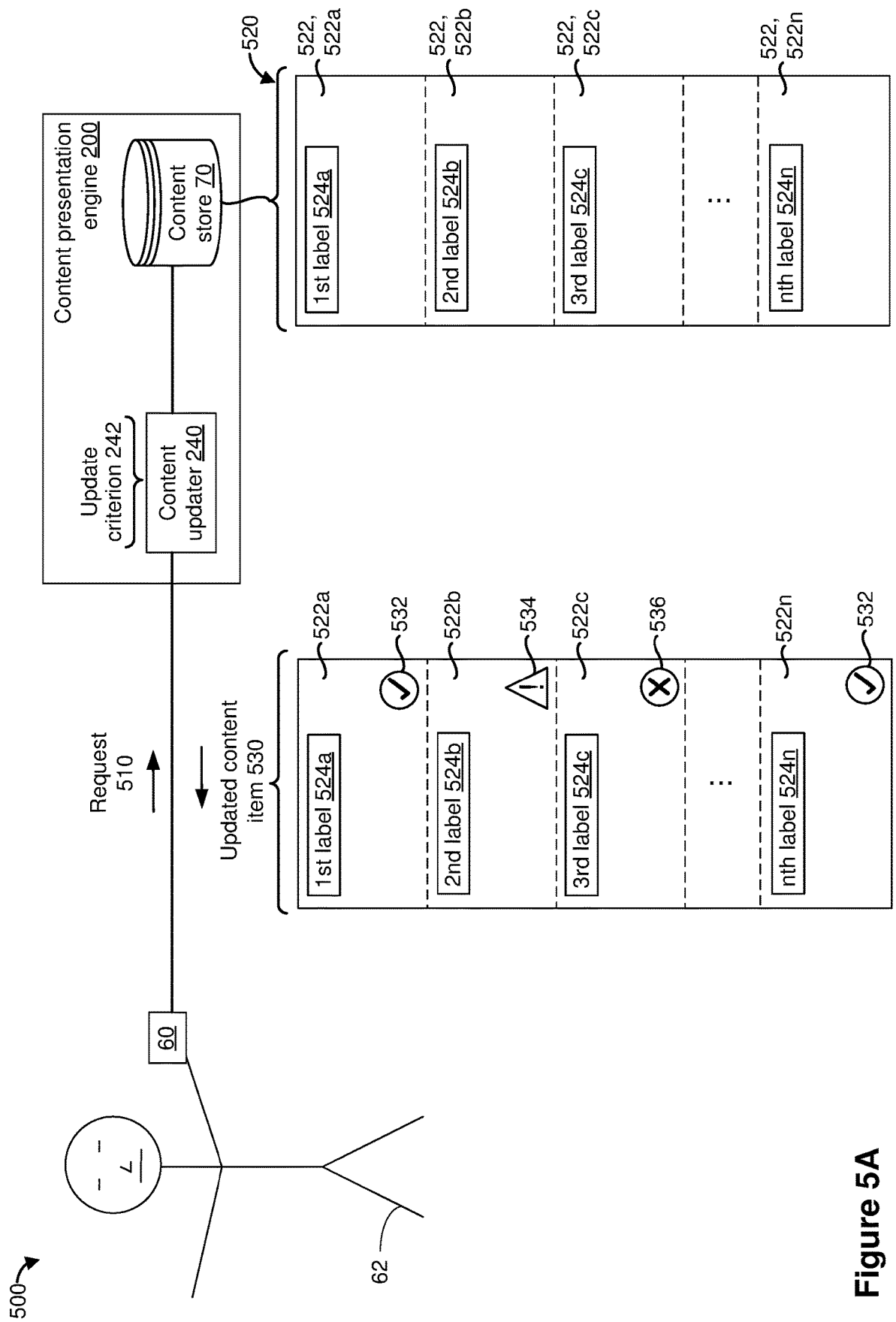
FIGS. 5A-5E are diagrams of another example operating environment in accordance with some implementations.

FIG. 5A is a diagram of an example operating environment 500 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 500 includes the electronic device 60 ("device 60", hereinafter for the sake of brevity), and at least a portion of the content presentation engine 200 shown in FIG. 2 (e.g., the content updater 240 and the content store 70).

As shown in FIG. 5A, in some implementations, the content store 70 stores a media content item 520 that provides information regarding a domain (e.g., a pharmaceutical article such as a pharmaceutical drug or a medical device). In some implementations, the media content item 520 includes various portions 522 (e.g., a first portion 522a, a second portion 522b, a third portion 522c, . . . , and an nth portion 522n) that provide information regarding various topics that are related to (e.g., a part of) the domain of the media content item 520. In some implementations, each of the portions 522 is associated with a respective label that indicates the topic(s) that the portion relates to. For example, the first portion 522a is associated with a first label 524a that indicates a first topic that the first portion 522a relates to (e.g., the first label 524a may be 'medical formulation' to indicate that the first portion 522a provides information regarding a medical formulation of a pharmaceutical drug). Similarly, the second portion 522b is associated with a second label 524b indicative of a second topic that the second portion 522b relates to (e.g., medical uses). The third portion 522c is associated with a third label 524c indicative of a third topic that the third portion 522c relates to (e.g., side effects), . . . , and the nth portion 522n is associated with an nth label 524n indicative of an nth topic that the nth portion 522n relates to.

In various implementations, the content presentation engine 200 (e.g., the content updater 240) obtains a request 510 from the device 60 to provide the media content item 520. In some implementations, the content presentation engine 200 (e.g., the content updater 240) determines whether the media content item 520 satisfies an update criterion 242. In some implementations, if the content presentation engine 200 (e.g., the content updater 240) determines that the media content item 520 satisfies the update criterion 242, the content updater 240 updates the media content item 520 in order to generate an updated media content item 530, and the content presentation engine 200 provides the updated media content item 530 to the device 60 (e.g., instead of the media content item 520). In some implementations, if the content presentation engine 200 determines that the media content item 520 does not satisfy the update criterion 242, the content presentation engine 200 provides the media content item 520 to the device 20 without updating the media content item 520.

In some implementations, the content updater 240 updates the media content item 520 by annotating the media content item 520 to indicate whether or not the portions 522 are up-to-date based on external information (e.g., information stored in a datastore and/or information provided by other more recent media content items). In the example of FIG. 5A, the updated media content item 530 includes two instances of an up-to-date indicator 532 to indicate that the first portion 522a and the nth portion are up-to-date (e.g., recent, accurate and/or valid). In some implementations, the up-to-date indicator 532 indicates that the information provided by the first portion 522a and the nth portion 522n is consistent with information stored in a datastore and/or with information provided by more recent media content items that relate to the same topics as the first portion 522a and the nth portion 522n.

In the example of FIG. 5A, the content updater 240 includes a warning indicator 534 in the second portion 522b of the updated media content item 530 to indicate that at least some of the information provided by the second portion 522b is outdated (e.g., stale, inaccurate, incomplete and/or not relevant). In some implementations, the content updater 240 includes the warning indicator 534 in the second portion 522b in response to determining that an amount of outdated information is below a threshold (e.g., less than 5%, 10%, 20%, etc.). In some implementations, the content updater 240 includes the warning indicator 534 in the second portion 522b in response to determining that a degree of outdatedness of the outdated information is less than a threshold degree (e.g., in response to determining that the outdated information in the second portion 522b is incomplete but not inaccurate).

In some implementations, the content updater 240 includes an invalid indicator 536 in the third portion 522c of the updated media content item 530 to indicate that an entirety of the information provided by the third portion 522c is outdated (e.g., stale, inaccurate, incomplete and/or not relevant). In some implementations, the content updater 240 includes the invalid indicator 53 in the third portion 522c in response to determining that an amount of outdated information in the third portion 522c is greater than a threshold (e.g., greater than 50%, 80%, 90%, etc.). In some implementations, the content updater 240 includes the invalid indicator 536 in the third portion 522c in response to determining that a degree of outdatedness of the outdated information in the third portion 522c is greater than a threshold degree (e.g., in response to determining that the information provided by the third portion 522c is inaccurate, misleading or fraudulent).

In some implementations, the content presentation engine 200 provides the updated media content item 530 to a content generation entity (not shown) that generated by the media content item 520. In some implementations, the content presentation engine 200 provides the content generation entity an option to modify the media content item 520 in order to remedy deficiencies that triggered the content updater 240 to include the warning indicator 534 and/or the invalid indicator 536 in the updated media content item 530. If the content generation entity modifies the media content item 520 to remedy the deficiencies that triggered the warning indicator 534 and/or the invalid indicator 536, the content presentation engine 200 removes the warning indicator 534 and/or the invalid indicator 536 and provides the device 60 with an updated version of the media content item 520 that the content generation entity provided. In some implementations, the content presentation engine 200 concurrently transmits the updated media content item 530 to the device 60 and the content generation entity in order to notify the content generation entity of the deficiencies that triggered the inclusion of the warning indicator 534 and the invalid indicator 536 into the updated media content item 530.

In some implementations, the content updater 240 determines whether or not a particular portion 522 of the media content item 520 satisfies the update criterion 242 by comparing information included in that particular portion 522 with information stored in a datastore's data field that corresponds to the label associated with that particular portion 522. For example, if the first label 524a is 'medical formulation', the content updater 240 compares the information in the first portion 522a with information stored in a data field that stores medical formulation information. In some implementations, if the information included in a particular portion 522 is different from the information stored in a data field that corresponds to the label associated with that particular portion 522, the content updater 240 determines that the particular portion 522 satisfies the update criterion 242. For example, if the first portion 522a provides information regarding medical formulation of a pharmaceutical drug and the information in the first portion 522a is different from information stored in a datastore's data field that stores medical formulation information, the content updater 240 determines that the first portion 522a satisfies the update criterion 242.

In some implementations, the content updater 240 determines whether or not a particular portion 522 of the media content item 520 satisfies the update criterion 242 by comparing information included in that particular portion 522 with information provided by other media content items that are related to the topic indicated by the label associated with that particular portion 522. For example, if the second label 524b is 'side effects', the content updater 240 compares the information in the second portion 522b with information provided by other media content items that discuss side effects of the pharmaceutical drug. In some implementations, if the information included in a particular portion 522 is different from the information provided by the related media content items, the content updater 240 determines that the particular portion 522 satisfies the update criterion 242. For example, if the second portion 522b provides information regarding side effects of a pharmaceutical drug and the information in the second portion 522b is different from information provided by other media content items that discuss side effects of the pharmaceutical drug, the content updater 240 determines that the second portion 522b satisfies the update criterion 242.

In various implementations, the content updater 240 utilizes the first label 524a to identify an information source (e.g., an external information source) that provides information regarding a topic associated with the first label 524a. For example, if the first label 524a is 'medical formulation', the content updater 240 identifies an information source that provides information regarding the medical formulation (e.g., the pharmacological composition) of the pharmaceutical drug. In some implementations, the information source is a datastore (e.g., the datastore 50 shown in FIGS. 1C-2, for example, a subset of the data fields 52 that store medical formulation data). Additionally or alternatively, in some implementations, the information source includes a set of media content items that provide information regarding the medical formulation of the pharmaceutical drug. In some implementations, the information source is controlled by an entity that is different from the content generation entity that generated the media content item 520.

In some implementations, the content updater 240 determines whether or not the first portion 522a satisfies the update criterion 242 by comparing information provided by the first portion 522a with information provided by the information source. In some implementations, if the information provided by the information source is different from the information included in the first portion 522a, the content updater 240 determines that the first portion 522a satisfies the update criterion 242. After determining that the first portion 522a satisfies the update criterion 242, the content updater 240 updates the first portion 522a based on the information included in the information source.

Since the content updater 240 utilizes the label associated with a portion 522 to identify an information source, the information sources for different portions 522 may be different. For example, the information source that the content updater 240 identifies using the first label 524a may include a first subset of the data fields 52 (shown in FIGS. 1C-2) or a first set of media content items that provide information regarding a first topic represented by the first label 524a, whereas the information source that the content updater 240 identifies using the second label 524b may include a second subset of the data fields 52 (shown in FIGS. 1C-2) or a second set of media content items that provide information regarding a second topic represented by the second label 524b.

In some implementations, the content updater 240 determines whether or not a particular portion 522 of the media content item 520 satisfies the update criterion 242 based on a date and/or a time associated with that particular portion 522. In some implementations, a portion 522 may be associated with an expiry date and/or an expiry time. In such implementations, if the expiry date is before a current date or the expiry time is before a current time, the content updater 240 determines that the portion 522 satisfies the update criterion 242 because the portion 522 includes information that may be expired (e.g., invalid). After determining that an expiry date and/or an expiry time associated with a portion 522 was in the past, the content updater 240 updates the portion 522 with information from an information source that is associated with an expiry date and/or an expiry time that is in the future thereby replacing potentially invalid information with valid information.

Figure 5B:
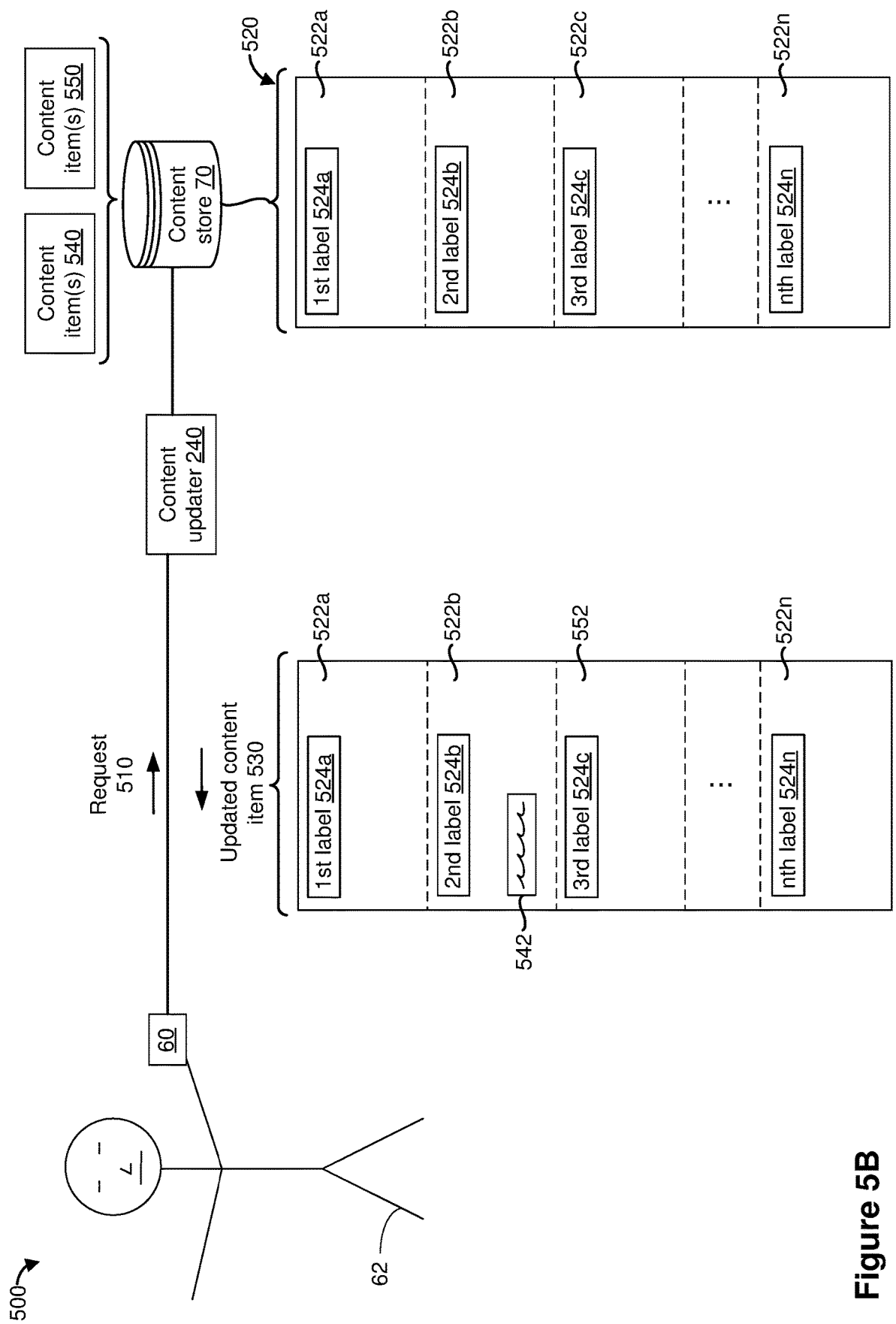

Referring to FIG. 5B, in some implementations, the content updater 240 determines that at least some of the information provided by the second portion 522b is outdated by comparing the information provided by the second portion 522b with information provided by a first information source (e.g., a first set of media content items 540) that provides information regarding the same topic as the second portion 522b. In some implementations, the content updater 240 utilizes the second label 524b to identify the first information source (e.g., the first set of media content items 540). For example, in some implementations, the content updater 240 uses the second label 524*b* as a search term in a search operation, and receives an indication of the first information source (e.g., the first set of media content items 540) as a search result. While the first set of media content items 540 is shown as an example of the first information source, in some implementations, the first information source includes a set of data fields in a datastore that store information regarding the same topic as the second portion 522*b* (e.g., a subset of the data fields 52 shown in FIGS. 1C-2).

As shown in FIG. 5B, in some implementations, the content updater 240 includes updated content 542 in the second portion 522*b*. In various implementations, the content updater 240 extracts the updated content 542 from the first information source (e.g., from the first set of media content items 540 and/or a set of data fields that store information regarding the same topic as the second portion 522*b*). In some implementations, since an amount and/or a degree of outdated information in the second portion 522*b* is less than a threshold, the content updater 240 forgoes removing information from the second portion 522*b*. In some implementations, since an amount and/or a degree of outdated information in the second portion 522*b* is less than a threshold, the content updater 240 forgoes replacing the second portion 522*b* in its entirety. In some implementations, since an amount and/or a degree of outdated information in the second portion 522*b* is less than a threshold, the content updater 240 forgoes deleting the second portion 522*b* in its entirety.

In some implementations, the content updater 240 sends the updated content 542 for the second portion 522*b* to a content generation entity that generated the media content item 520. The content updater 240 can send the updated content 542 to the content generation entity as a proposed modification to the media content item 520. The content updater 240 can provide the content generation entity with options to accept the proposed modification or reject the proposed modification. In some implementations, if the content generation entity accepts the proposed modification, the content updater 240 includes the updated content 542 in the second portion 522*b*. However, in some implementations, if the content generation entity rejects the proposed modification, the content updater 240 includes the warning indicator 534 (shown in FIG. 5A) instead of including the updated content 542. In some implementations, the content updater 240 sends proposed modifications to the content generation entity if the content generation entity subscribes to receive proposed modifications and/or provides electronic credit data for receiving proposed modifications. In some implementations, allowing the content generation entity to approve or reject the updated content 542 provides the content generation entity control over the media content item 520 that the content generation entity generated. In some implementations, providing the content generation entity control over the media content item 520 tends to maintain at least an appearance of authenticity of the media content item 520.

In the example of FIG. 5B, the content updater 240 determines that the information provided by the third portion 522*c* is outdated by comparing the information provided by the third portion 522*c* with information provided by a second information source (e.g., a second set of media content items 550) that provides information regarding the same topic as the third portion 522*c*. In some implementations, the content updater 240 utilizes the third label 524*c* to identify the second information source (e.g., the second set of media content items 550). For example, in some implementations, the content updater 240 uses the third label 524*c* as a search term in a search operation, and receives the second information source (e.g., the second set of media content items 550) as a search result. While the second set of media content items 550 is shown as an example of the second information source, in some implementations, the second information source includes a set of data fields in a datastore that stores information regarding the same topic as the third portion 522*c* (e.g., a subset of the data fields 52 shown in FIGS. 1C-2).

As shown in FIG. 5B, in some implementations, the content updater 240 replaces the third portion 522*c* with a replacement portion 552. In various implementations, the content updater 240 synthesizes (e.g., generates) the replacement portion 552 based on information extracted from the second information source (e.g., from the second set of media content items 550 and/or a set of data fields that store information regarding the same topic as the third portion 522*c*). In some implementations, the content updater 240 replaces the third portion 522*c* in its entirety (e.g., instead of modifying the third portion 522*c* incrementally) in response to determining that an amount and/or a degree of outdated information in the third portion 522*c* is greater than a threshold.

Figure 5C:
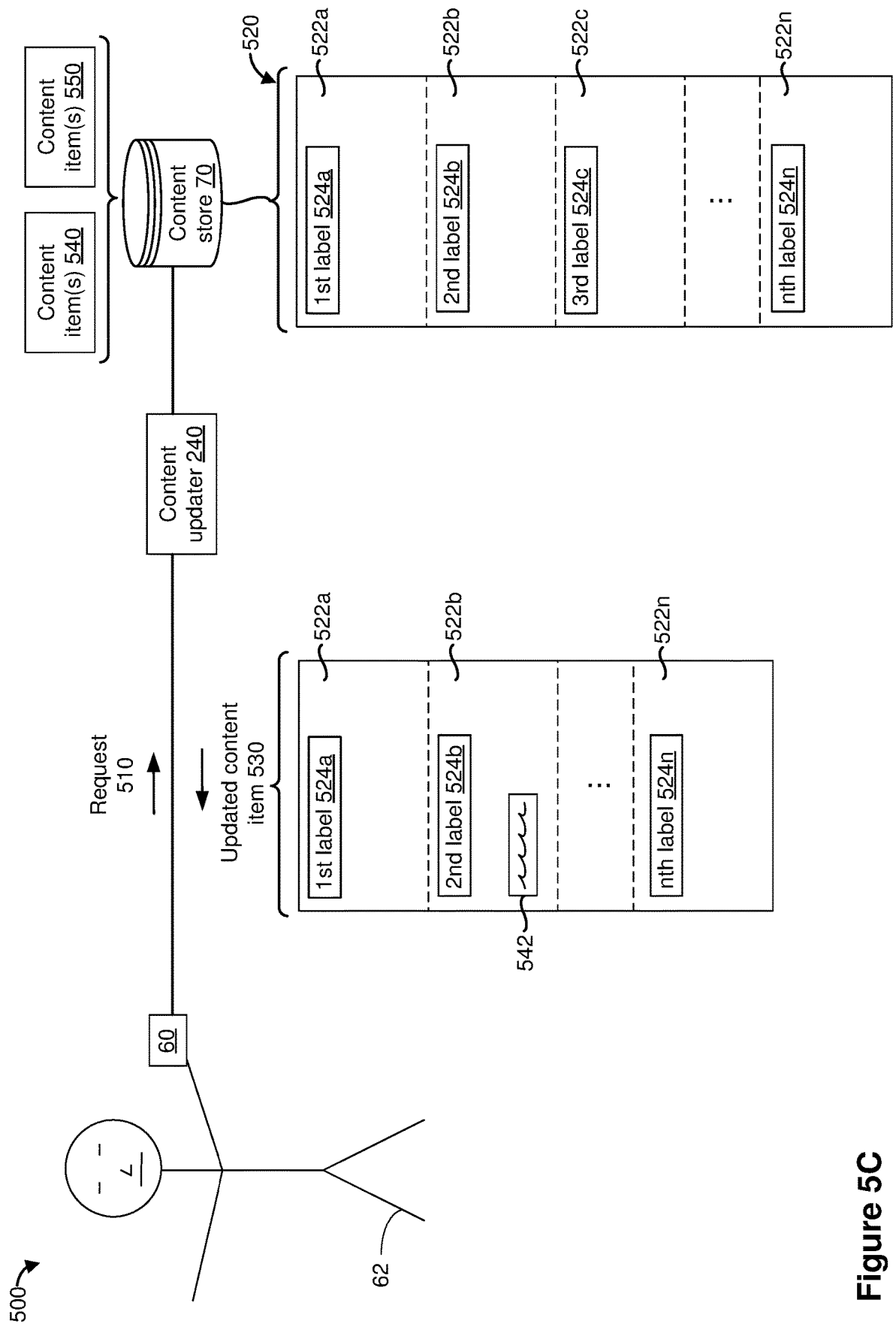

Referring to FIG. 5C, in some implementations, the content updater 240 removes (e.g., deletes) the third portion 522*c* in its entirety in response to determining that an amount and/or a degree of outdated information in the third portion exceeds a threshold. For example, in some implementations, the content updater 240 removes the third portion 522*c* from the media content item 520 in response to an amount of inaccurate information in the third portion 522*c* exceeding an inaccuracy threshold (e.g., in response to an amount of inaccurate information being greater than 50%, 80%, 90%, etc.).

In some implementations, the content updater 240 sends the replacement portion 552 (shown in FIG. 5B) for the third portion 522*c* to a content generation entity that generated the media content item 520. The content updater 240 can send the replacement portion 552 to the content generation entity as a proposed modification to the media content item 520. The content updater 240 can provide the content generation entity with options to accept the proposed modification or reject the proposed modification. In some implementations, if the content generation entity accepts the proposed modification, the content updater 240 replaces the third portion 522*c* with the replacement portion 552. In some implementations, if the content generation entity rejects the proposed modification, the content updater 240 removes the third portion 522*c* (as shown in FIG. 5B). In some implementations, the content updater 240 sends proposed modifications to the content generation entity if the content generation entity subscribes to receive proposed modifications and/or provides electronic credit data for receiving proposed modifications.

Figure 5D:
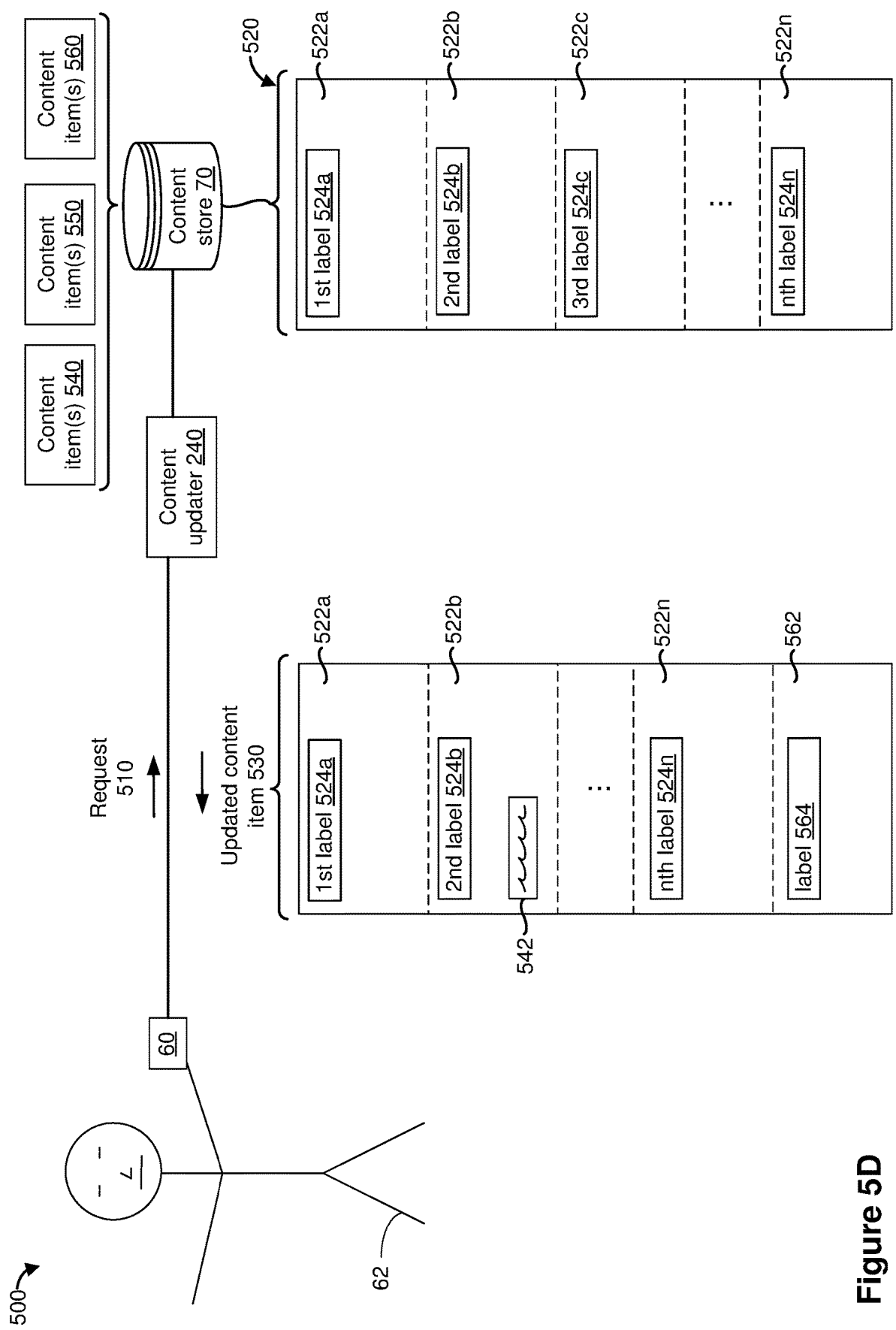

Referring to FIG. 5D, in some implementations, the updated media content item 530 includes a new portion 562 that the media content item 520 does not include. As shown in FIG. 5D, the content updater 240 generates and associates a new label 564 with the new portion 562 in order to indicate a topic that the new portion 562 relates to. In some implementations, the topic that the new portion 562 relates to is different from topics that the existing portions 522*a*, 522*b*, . . . , and 522*n* relate to. In some implementations, the content updater 240 synthesizes the new portion 562 based on information included in a third set of media content items 560 that did not exist when the media content item 520 was generated. In some implementations, the content updater 240 sends the new portion 562 to the content generation entity that generated the media content item 520 as a proposed modification. In some implementations, the content updater 240 includes the new portion 562 in the updated media content item 530 in response to the content generation entity approving the inclusion of the new portion 562 in the updated media content item 530. In some implementations, the content updater 240 forgoes including the new portion 562 in the updated media content item 530 in response to the content generation entity rejecting the inclusion of the new portion 562 in the updated media content item 530. Although the new portion 562 is shown as being appended to an end of the media content item 520 (e.g., after the nth portion 522n), in some implementations, the content updater 240 inserts the new portion 562 between two of the existing portions 522 (e.g., between the first portion 522a and the second portion 522b).

Although FIG. 5D illustrates the content updater 240 obtaining information for the new portion 562 from the third set of media content items 560, more generally, in various implementations, the content updater 240 obtains the information for the new portion 562 from an information source that did not exist when the media content item 520 was generated. For example, in some implementations, the content updater 240 obtains the information for the new portion 562 from a datastore's data fields that did not exist or did not include any information when the media content item 520 was generated by the content generation entity. In various implementations, adding the new portion 562 to the media content item 520 allows the media content item 520 to automatically expand over time as new information becomes available (e.g., as new information regarding a pharmaceutical drug is discovered, for example, as additional side effects of the pharmaceutical drug are reported by patients or as additional medical uses for the pharmaceutical drug as discovered by clinicians).

Figure 5E:
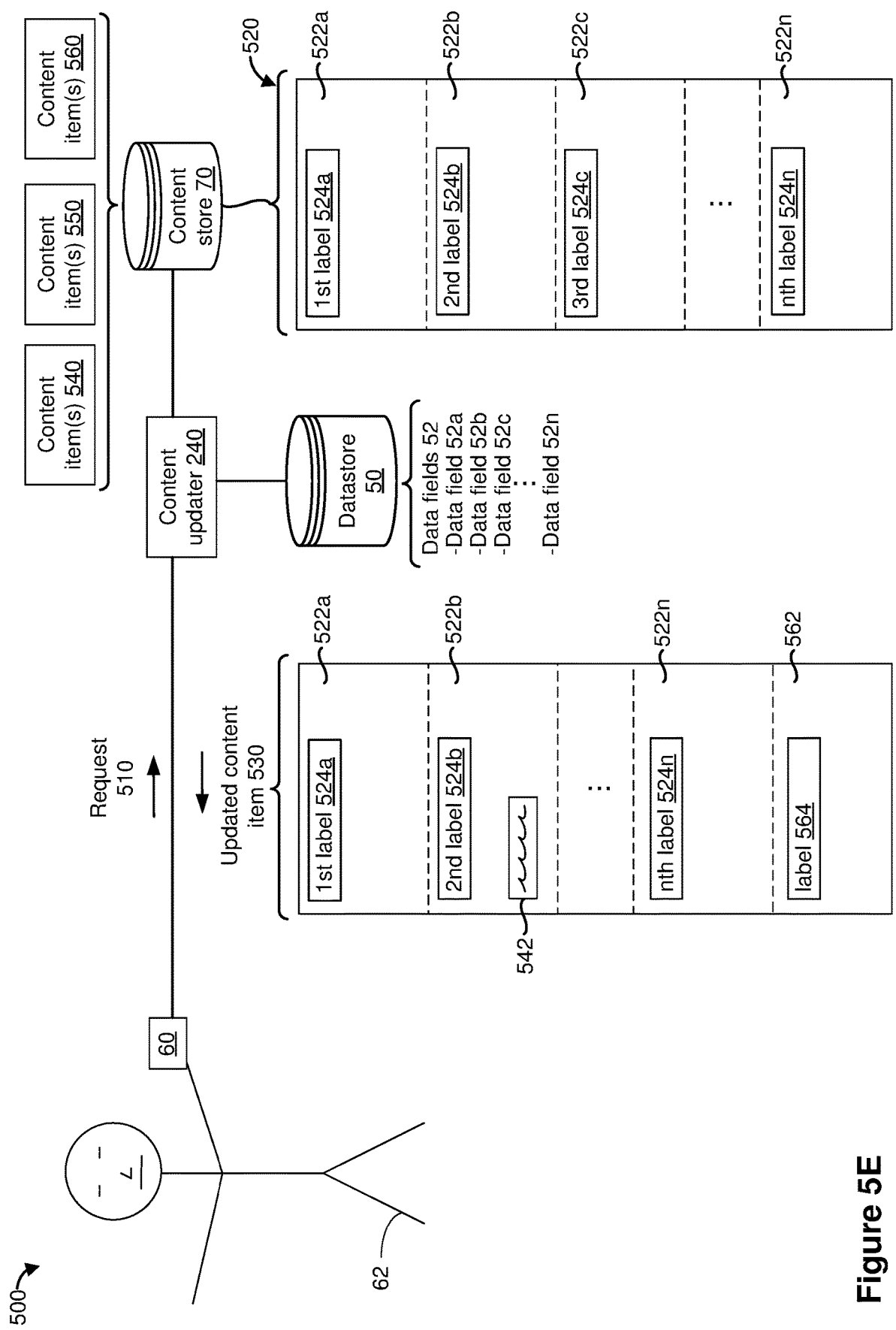

Referring to FIG. 5E, as described herein, in some implementations, the content updater 240 utilizes information stored in association with the data fields 52 in the datastore 50 to modify the media content item 520 and generate the updated media content item 530. In various implementations, the data fields 52 store the information provided by the first set of media content items 540, the second set of media content items 550 and/or the third set of media content items 560. As such, instead of extracting the information directly from the first set of media content items 540, the second set of media content items 550 and/or the third set of media content items 560, the content updater 240 retrieves the information from the datastore 50.

In some implementations, the content updater 240 stores the updated media content item 530 in the content store 70. In some implementations, the content updater 240 replaces the media content item 520 in the content store 70 with the updated media content item 530. In some implementations, when a user subsequently requests the media content item 520, the content presentation engine 200 retrieves the updated media content item 530 from the content store 70 and provides the updated media content item 530 to the user.

Figure 6:
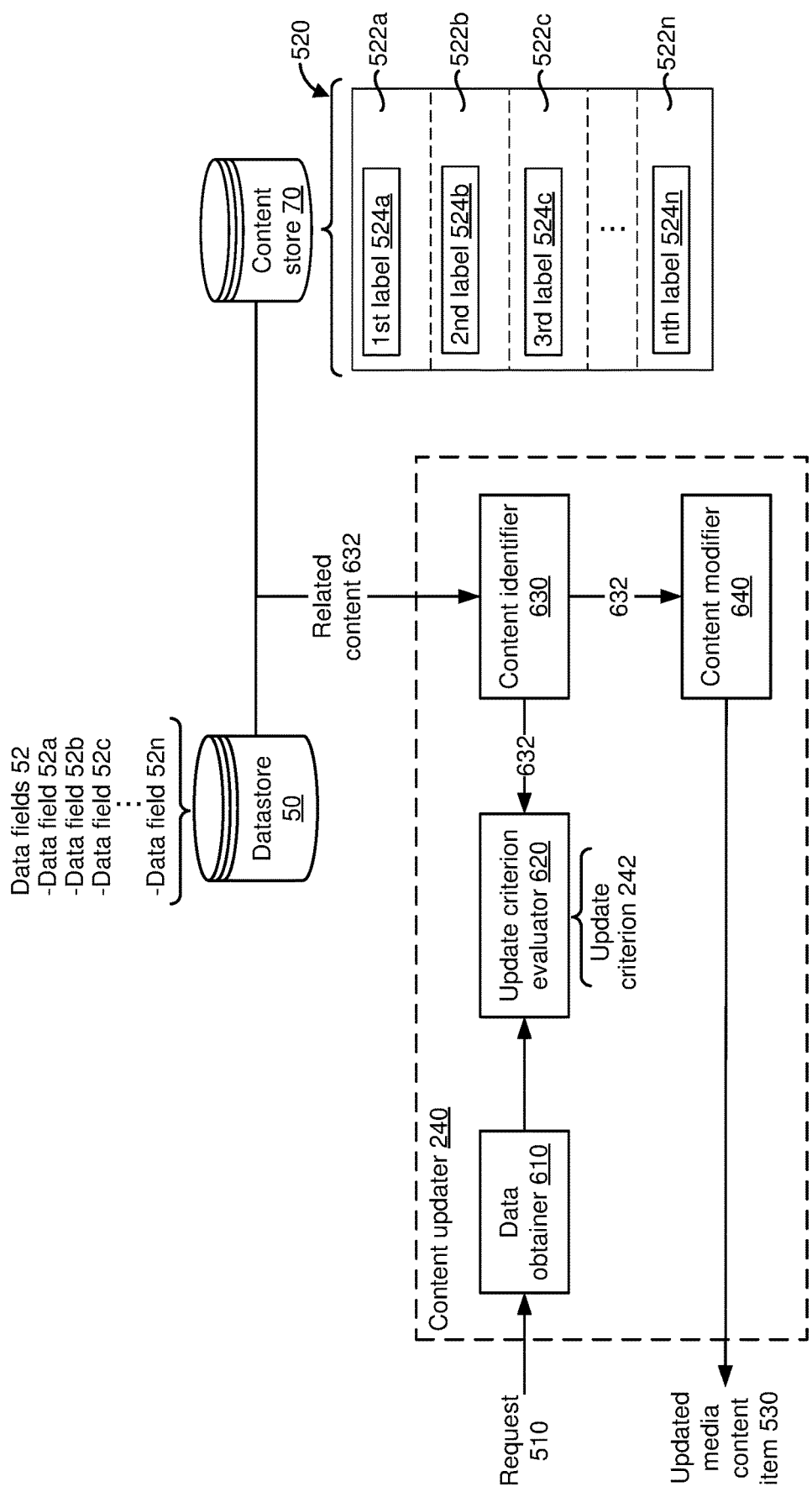
FIG. 6 is another block diagram of the content presentation engine in accordance with some implementations.

FIG. 6 illustrates a block diagram of the content updater 240 in accordance with some implementations. In some implementations, the content updater 240 includes a data obtainer 610, an update criterion evaluator 620, a content identifier 630, and a content modifier 640. In some implementations, the data obtainer 610 obtains (e.g., receives or retrieves) and interprets the request 510. In some implementations, the data obtainer 610 provides the update criterion evaluator 620 an indication that the request 510 is associated with the media content item 520.

In various implementations, the update criterion evaluator 620 determines whether the media content item 520 satisfies the update criterion 242. In some implementations, the update criterion evaluator 620 evaluates each portion 522 of the media content item 520 in relation to the update criterion 242. In some implementations, the update criterion 242 includes multiple update criteria, and the update criterion evaluator 620 determines that the media content item 520 satisfies the update criterion 242 in response to at least one of the multiple update criteria being satisfied.

In some implementations, the content identifier 630 identifies content 632 that is related to the media content item 520 ("related content 632", hereinafter for the sake of brevity). In some implementations, the content identifier 630 uses the labels 524 to identify the related content 632. For example, in some implementations, the content identifier 630 identifies content related to the first portion 522a by searching the datastore 50 and/or the content store 70 for content that matches the first label 524a. Similarly, in some implementations, the content identifier 630 identifies content related to the second portion 522b by searching the datastore 50 and/or the content store 70 for content that matches the second label 524b. In some implementations, the content identifier 630 provides the related content 632 to the update criterion evaluator 620 and/or to the content modifier 640.

In some implementations, the update criterion evaluator 620 determines whether a portion 522 satisfies the update criterion 242 by comparing the information included in the portion 522 with information included in the related content 632. In some implementations, if the information included in portion 522 is different from the information included in the related content 632 and the related content 632 is more recent than the media content item 520, the update criterion evaluator 620 determines that the portion satisfies the update criterion 242. In some implementations, if the information included in the portion 522 is different from the information included in the related content 632 and the related content 632 is more reliable than the media content item 520 (e.g., the related content 632 has been cited more times than the media content item 520), the update criterion evaluator 620 determines that the portion satisfies the update criterion 242.

In some implementations, the update criterion 242 includes a recency threshold that specifies an amount of time (e.g., a number of years). In some implementations, if a portion 522 of the media content item 520 was generated prior to the recency threshold (e.g., more than the number of years specified by the recency threshold), the update criterion evaluator 620 determines that the portion 522 satisfies the update criterion 242. In some implementations, a portion 522 that was generated prior to the recency threshold is considered stale, and the content modifier 640 updates the portion 522 in order to increase a currentness score of the portion 522. More generally, in some implementations, the update criterion evaluator 620 determines that a portion 522 breaches the update criterion 242 in response to a recency score of the portion 522 breaching (e.g., being less than) a threshold recency score specified by the update criterion 242. In some implementations, the recency score of the portion 522 is a function of a date and/or a time when the portion 522 was created and/or last updated.

In some implementations, the update criterion 242 includes a reliability threshold that specifies a threshold number. In some implementations, if a portion 522 of the media content item 520 has been criticized or debunked a number of times that is greater than the threshold number specified by the reliability threshold, the update criterion evaluator 620 determines that the portion 522 satisfies the update criterion 242. In some implementations, a portion 522 that has been criticized or debunked more than the threshold number of times may be unreliable, and the content modifier 640 updates the portion 522 in order to increase a reliability score of the portion 522. More generally, in some implementations, the update criterion evaluator 620 determines that a portion 522 breaches the update criterion 242 in response to a reliability score of the portion 522 breaching (e.g., being less than) a threshold reliability score specified by the update criterion 242. In some implementations, the reliability score of the portion 522 is a function of a number of times that the portion 522 has been criticized or debunked by the related content 632.

In some implementations, the update criterion evaluator 620 provides an indication to the content modifier 640 that a portion 522 satisfies the update criterion 242. In some implementations, the content modifier 640 utilizes the related content 632 to update the portion 522. For example, in some implementations, the content modifier 640 modifies the portion 522 to remove information that is associated with a reliability score that breaches (e.g., is less than) a threshold reliability score, a recency score that breaches a threshold recency score and/or an accuracy score that breaches a threshold accuracy score. In some implementations, the content modifier 640 replaces the portion 522 with a replacement portion (e.g., as discussed in relation to FIG. 5C). In some implementations, the content modifier 640 removes the portion 522 from the media content item 520 (e.g., as discussed in relation to FIG. 5C). In some implementations, modifying one or more portions 522 of the media content item 520 results in the updated media content item 530. In some implementations, the content modifier 640 provides the updated media content item 530 to the electronic device 60 that generated the request 510. Additionally, in some implementations, the content modifier 640 stores the updated media content item 530 in the content store 70. For example, in some implementations, the content modifier 640 replaces the media content item 520 with the updated media content item 530.

Figure 7:
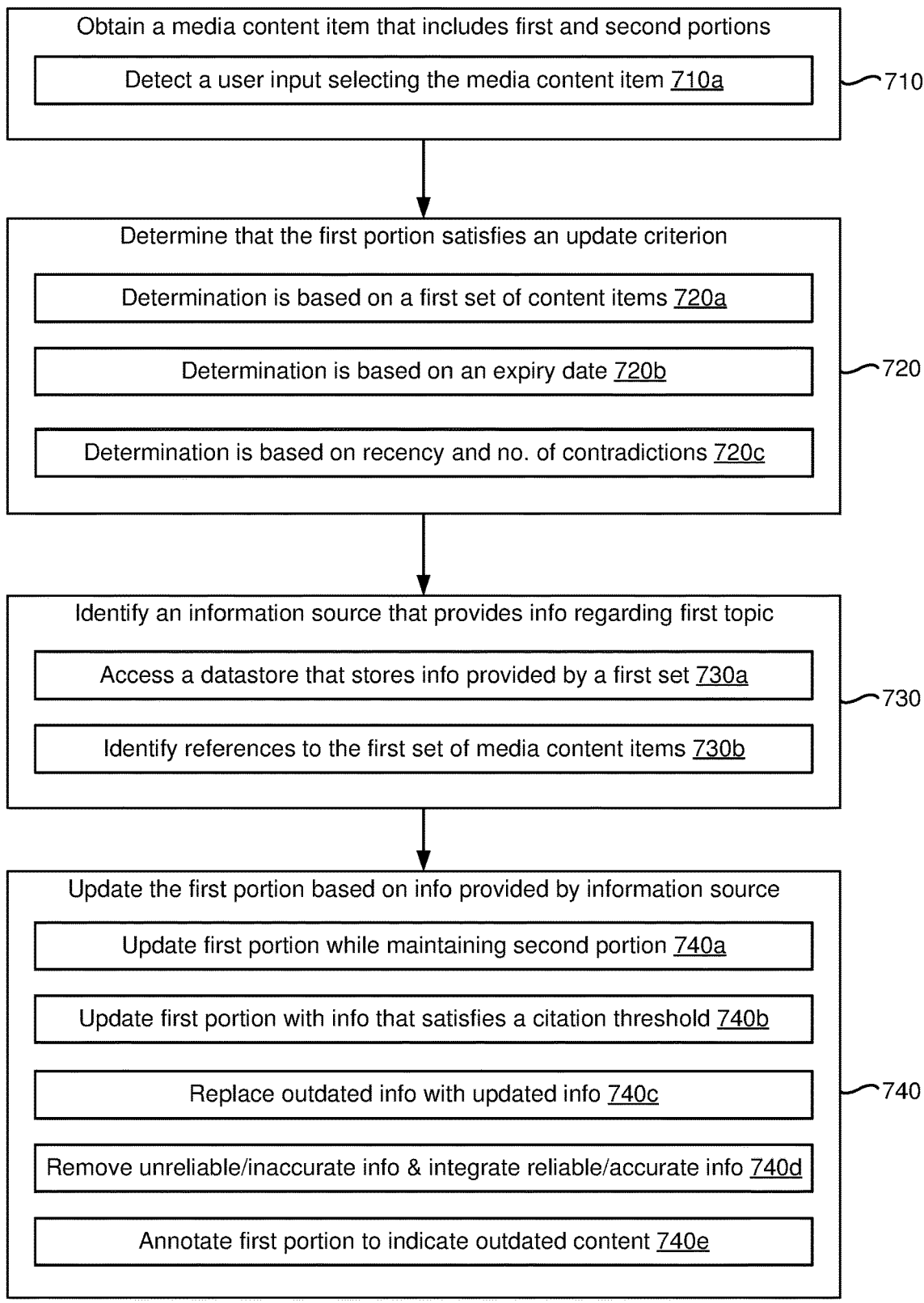
FIG. 7 is a flowchart representation of a method of updating a media content item in accordance with some implementations.

FIG. 7 is a flowchart representation of a method 700 of updating a pharmaceutical content item in accordance with some implementations. In various implementations, the method 700 is performed by a device including a non-transitory memory and a processor coupled with the non-transitory memory (e.g., the device 20 shown in FIGS. 1A-1E, the content presentation engine 200 shown in FIGS. 2 and 5A, and/or the content updater 240 shown in FIGS. 2 and 5A-6). In some implementations, the method 700 is performed by processing logic, including hardware, firmware, software, or a combination thereof. In some implementations, the method 700 is performed by a processor executing code stored in a non-transitory computer-readable medium (e.g., a memory). In some implementations, the method 700 is performed by a server. In some implementations, the method 700 is performed at a cloud computing platform. In some implementations, the method 700 is performed by a portable electronic device (e.g., the electronic device 60 shown in FIGS. 5A-5E).

As represented by block 710, in various implementations, the method 700 includes obtaining a pharmaceutical content item that includes a plurality of portions associated with respective topic labels indicative of pharmaceutical topics that the plurality of portions provides information regarding.

In some implementations, the plurality of portions includes a first portion that is associated with a first topic label indicative of a first pharmaceutical topic and a second portion that is associated with a second topic label indicative of a second pharmaceutical topic. For example, as shown in FIGS. 5A-6, the media content item 520 includes the first portion 522a that is associated with the first label 524a indicative of the first topic that the first portion 522a relates to, and the media content item 520 includes the second portion 522b that is associated with the second label 524b indicative of the second topic that the second portion 522b relates to.

As represented by block 710a, in some implementations, obtaining the pharmaceutical content item includes detecting a user input selecting the pharmaceutical content item from a plurality of pharmaceutical content items. In some implementations, the method 700 includes receiving a selection request for the pharmaceutical content item. In some implementations, the method 700 includes generating the respective topic labels for the plurality of portions based on information provided by the plurality of portions (e.g., as described in relation to FIGS. 1A-4).

As represented by block 720, in various implementations, the method 700 includes determining that the first portion satisfies an update criterion. For example, as discussed in relation to FIG. 6, the update criterion evaluator 620 determines that a portion 522 of the media content item 520 satisfies the update criterion 242. In some implementations, the update criterion includes multiple criteria (e.g., a recency criterion, a reliability criterion, an expiry date criterion and/or an accuracy criterion), and the device determines that the first portion satisfies the update criterion in response to the first portion satisfying at least one of the multiple update criteria.

As represented by block 720a, in some implementations, determining that the first portion satisfies the update criterion comprises determining that the first portion satisfies the update criterion based on the information provided by the information source. For example, as described in relation to FIG. 5B, the content updater 240 determines that the second portion 522b satisfies the update criterion 242 based on information included in the first set of media content items 540 that provides information related to the second topic, and the content updater 240 determines that the third portion 522c satisfies the update criterion 242 based on information included in the second set of media content items 550 that provides information related to the third topic.

In some implementations, the information source includes a first set of one or more pharmaceutical content items that provides information regarding the first topic. For example, as described in relation to FIG. 5B, the content updater 240 identifies the first set of media content items 540 based on the second label 524b associated with the second portion 522b of the media content item 520. In some implementations, determining that the first portion satisfies the update criterion includes detecting a change in the information provided by the first set of one or more pharmaceutical content items, and determining that the first portion satisfies the update criterion in response to detecting the change in the information provided by the first set of one or more pharmaceutical content items. As an example, referring to FIG. 5B, the content updater 240 determines that the second portion 522b satisfies the update criterion 242 in response to detecting a change in the first set of media content items 540. Advantageously, as information regarding the first topic changes, the first portion is automatically updated in order to maintain a currentness of the first portion.

In some implementations, detecting the change in the first set of one or more pharmaceutical content items comprises detecting an addition of a pharmaceutical content item to the first set of one or more pharmaceutical content items. As an example, referring to FIG. 5B, the content updater 240 determines that the second portion 522b satisfies the update criterion 242 in response to detecting that the first set of media content items 540 includes a new media content item that the first set of media content items 540 did not include when the second portion 522b of the media content item 520 was initially created. Advantageously, as new information regarding the first topic becomes available, the first portion is automatically updated based on the new information in order to keep the media content item updated.

In some implementations, detecting the change in the first set of one or more pharmaceutical content items comprises detecting a removal of a pharmaceutical content item from the first set of one or more pharmaceutical content items. As an example, referring to FIG. 5B, the content updater 240 determines that the second portion 522b satisfies the update criterion 242 in response to detecting that a media content item that was in the first set of media content items 540 when the second portion 522b was initially created is no longer a part of the first set of media content items 540 (e.g., because the media content item was removed/deleted due to including information that is no longer considered accurate) Advantageously, as some information regarding the first topic is invalidated (e.g., proven to be false), the first portion is automatically updated to remove the invalid information in order to maintain an accuracy of the media content item.

In some implementations, detecting the change in the first set of one or more pharmaceutical content items comprises detecting an update to at least one of the pharmaceutical content items in the first set of one or more pharmaceutical content items. As an example, referring to FIG. 5B, in some implementations, the first set of media content items 540 includes an FDA label, and as the FDA label is updated the second portion 522b of the media content item 520 is updated based on the updates to the FDA label. In some implementations, the pharmaceutical content item includes information regarding the first pharmaceutical topic from a source material (e.g., an FDA label), and as the source material is updated, the pharmaceutical content item is automatically updated to reflect changes to the source material.

In some implementations, detecting the change in the first set of one or more pharmaceutical content items comprises detecting a change in a data field of a datastore that stores the information from the first set of one or more pharmaceutical content items, and determining that the first portion satisfies the update criterion in response to detecting the change in the data field of the datastore. For example, as discussed in relation to FIGS. 5E and 6, the content updater 240 updates the second portion 522b of the media content item 520 based on information stored in association with a subset of the data fields 52 that relates to the second topic. In some implementations, referencing a structured datastore allows the pharmaceutical content item to be updated more readily. For example, the device conserves computing resources associated with extracting information from an unstructured data source such as an unlabeled document.

As represented by block 720b, in some implementations, determining that the first portion satisfies the update criterion comprises determining that the first portion satisfies the update criterion when an expiry date associated with the first portion occurs in the past. As an example, referring to FIG. 5A, in some implementations, the content updater 240 determines that an expiry date associated with the third portion 522c occurs in the past. As such, the content updater 240 annotates the third portion 522c to include the invalid indicator 536 in order to indicate that the third portion 522c includes information that may no longer be valid. Advantageously, updating information that is invalid increases a likelihood of maintaining a validity of the media content item.

In some implementations, determining that the first portion satisfies the update criterion comprises determining that the first portion satisfies the update criterion in response to the first portion including information from a pharmaceutical content item that is associated with an expiry date that occurs in the past. For example, if a portion of the pharmaceutical content item includes information from an FDA label with an expiry date that occurs in the past, the device determines that the portion satisfies the update criterion. Advantageously, updating expired information with unexpired information or indicating expired information reduces a likelihood of reliance on expired information and/or reduces a likelihood of spreading misinformation.

As represented by block 720c, in some implementations, determining that the first portion satisfies the update criterion comprises determining that the first portion satisfies the update criterion in response to the information source being associated with a first date that occurs after a second date associated with the first portion and the information source providing information that contradicts information included in the first portion. As an example, referring to FIG. 5B, the content updater 240 determines that the second portion 522b satisfies the update criterion 242 in response to the first set of media content items 540 including information that is different from (e.g., information that contradicts) the information provided by the second portion 522b and the second portion 522b being older than the first set of media content items 540 (e.g., the second portion 522b having being created before the first set of media content items 540 were created). In various implementations, the method 700 includes increasing a recency of the pharmaceutical content item by replacing stale information (e.g., old information, for example, information that was generated more than a threshold time ago) with more recent information (e.g., new information, for example, information that was generated less than a threshold time ago).

As represented by block 730, in various implementations, the method 700 includes utilizing the first topic label to identify an information source that provides information regarding the first pharmaceutical topic. For example, as described in relation to FIG. 5B, the content updater 240 utilizes the second label 524b to identify the first set of media content items 540 that provides information regarding the same topic as the second portion 522b, and the content updater 240 utilizes the third label 524c to identify the second set of media content items 550 that provides information regarding the same topic as the third portion 522c. In some implementations, the information source is referred to as an external source, for example, because the information source is different from the media content item that is being updated. In some implementations, the information source is different from a content generation entity that generated the media content item that is being updated. In some implementations, the information source includes a subset of data fields in a datastore (e.g., a subset of the data fields 52 shown in FIGS. 5E and 6). More generally, in some implementations, the information source includes a structured data set.

Alternatively, in some implementations, the information source included an unstructured data set (e.g., a free-flowing text in a document).

As represented by block 730a, in some implementations, identifying the information source comprises identifying a first set of one or more pharmaceutical content items that provides information regarding the first pharmaceutical topic, or identifying data fields of a datastore that store the information regarding the first pharmaceutical topic. In some implementations, the data fields store information that was extracted from the first set of one or more pharmaceutical content items. As described in relation to FIG. 5B, the content updater 240 identifies the first set of media content items 540 that provides information regarding the same topic as the second portion 522b of the media content item 520. As another example, referring to FIG. 5E, the content updater 240 identifies a first subset of the data fields 52 that provides information regarding the first topic, a second subset of the data fields 52 that provides information regarding the second topic, . . . , and an nth subset of the data fields 52 that provides information regarding the nth topic.

As represented by block 730b, in some implementations, identifying the first set of one or more pharmaceutical content items comprises identifying references to the first set of one or more pharmaceutical content items in the first portion. For example, in some implementations, the pharmaceutical content item refers to the FDA label for a pharmaceutical drug that the pharmaceutical content item relates to. In such implementations, the device retrieves the most recent version of the FDA label in order to compare the pharmaceutical content item with the most recent version of the FDA label. Since the pharmaceutical content item may include information from a previous version of the FDA label, some of the information in the pharmaceutical content item may be outdated in comparison to the most recent version of the FDA label. In some implementations, the pharmaceutical content item refers to a particular pharmaceutical content item in the first set as a whole or the pharmaceutical content item refers to a specific portion of the pharmaceutical content item in the first set. Identifying source material allows the device to update the media content item when there are changes to the source material thereby increasing a likelihood of the media content item being current and staying consistent with the source material.

As represented by block 740, in some implementations, the method 700 includes updating the first portion based on the information provided by the information source. In some implementations, the method 700 includes updating the first portion automatically (e.g., without the need for a human operator to generate an update for the first portion). As described herein, in some implementations, the information source includes a first set of one or more pharmaceutical content items (e.g., as discussed in relation to FIG. 5B, the information source for updating the second portion 522b is the first set of media content items 540). In some implementations, the method 700 includes updating the first portion of the pharmaceutical content item periodically. Additionally or alternatively, in some implementations, the method 700 includes updating the first portion of the pharmaceutical content item in response to detecting a user request to view the pharmaceutical content item.

In various implementations, updating the first portion of the pharmaceutical content item based on information provided by the information source (e.g., the first set of one or more pharmaceutical content items or a set of data fields that store information provided by the first set of one or more pharmaceutical content items) tends to enhance a user experience of the device by increasing an accuracy score, a currentness score and/or a relevance score of the first portion of the pharmaceutical content item. Updating the first portion of the pharmaceutical content item based on information provided by the information source (e.g., the first set of one or more pharmaceutical content items) tends to improve operability of the device by reducing power consumption associated with processing unnecessary user inputs that correspond to the user attempting to verify the accuracy and/or currentness of information provided by the first portion of the pharmaceutical content item.

As represented by block 740a, in some implementations, the method 700 includes updating the first portion while maintaining (e.g., forgoing an update to) the second portion of the plurality of portions in response to a determination, based on a second information source (e.g., a second set of one or more media content items) that provides information regarding the second pharmaceutical topic corresponding to the second topic label, that the second portion does not satisfy the update criterion. As an example, referring to FIG. 5B, the content updater 240 updates the second portion 522b while forgoing an update to the first portion 522a of the media content item 520.

As represented by block 740b, in some implementations, updating the first portion comprises updating the first portion with information, from the information source, that has been cited at least a threshold number of times. Information that has been cited a threshold number of times is more likely to be trustworthy (e.g., reliable) than information that has not been cited. Hence, updating the pharmaceutical content item with information that has been cited a threshold number of times tends to increase a trustworthiness (e.g., a reliability score) of the media content item thereby increasing a likelihood of the user engaging with the pharmaceutical content item due to the increase in trustworthiness (e.g., reliability).

As represented by block 740c, in some implementations, updating the first portion comprises replacing outdated information in the first portion with updated information from the information source. In some implementations, the method 700 includes replacing an entirety of the first portion with a replacement portion (e.g., as shown in FIG. 5B, the content updater 240 replaces the third portion 522c with the replacement portion 552). Advantageously, in various implementations, replacing outdated information with updated information tends to increase a currentness score of the pharmaceutical content item thereby increasing a likelihood of the user engaging with the pharmaceutical content item due to the increase in currentness.

As represented by block 740d, in some implementations, updating the first portion comprises removing, from the first portion, information that breaches a reliability threshold, and integrating, into the first portion, information from the information source that satisfies the reliability threshold. Advantageously, in some implementations, replacing unreliable information (e.g., information with a reliability score that is less than a threshold reliability score) with reliable information (e.g., information with a reliability score that is greater than the threshold reliability score) tends to increase a relevance score and/or a reliability score of the pharmaceutical content item thereby increasing a likelihood of the user engaging with the pharmaceutical content item due to the increase in relevance and/or the reliability.

As represented by block 740d, in some implementations, updating the first portion comprises removing, from the first portion, information that breaches an accuracy threshold, and integrating, into the first portion, information from the information source that satisfies the accuracy threshold. Advantageously, in some implementations, replacing inaccurate information (e.g., information with an accuracy score that is less than a threshold accuracy score) with accurate information (e.g., information with an accuracy score that is greater than the threshold accuracy score) tends to increase an accuracy score of the pharmaceutical content item thereby increasing a likelihood of the user engaging with the media content item due to the increase in accuracy.

As represented by block 740e, in some implementations, updating the first portion includes annotating the first portion in order to indicate that the first portion is outdated (e.g., stale, unreliable, incomplete and/or inaccurate). For example, as shown in FIG. 5A, the content updater 240 annotates the updated media content item 530 to include the warning indicator 534 and/or the invalid indicator 536.

In some implementations, the first portion of the pharmaceutical content item specifies dosage information (e.g., a dose amount and/or a dose frequency) for a pharmaceutical drug. In some implementations, the information source includes a pharmaceutical information source that provides updated dosage information for the pharmaceutical drug. In some implementations, the method 700 includes replacing the dosage information in the first portion with the updated dosage information provided by the pharmaceutical information source.

In some implementations, the first portion of the pharmaceutical content item specifies a first set of medical conditions for which a pharmaceutical drug is to be prescribed. In some implementations, the information source includes a pharmaceutical information source that specifies a second set of medical conditions for which the pharmaceutical drug is to be prescribed. In some implementations, the method 700 includes updating the first portion to specify the second set of medical conditions instead of or in addition to specifying the first set of medical conditions.

In some implementations, the first portion of the pharmaceutical content item specifies pharmaceutical advantages of a pharmaceutical article (e.g., pharmacological advantages of a pharmaceutical drug) over other comparable pharmaceutical articles. In some implementations, the information source includes a pharmaceutical information source that specifies additional advantages of the pharmaceutical article over the other comparable pharmaceutical articles. In some implementations, the method 700 includes updating the first portion of the pharmaceutical content item by including the additional advantages specified by the information source into the first portion of the pharmaceutical content item.

In some implementations, the first portion of the pharmaceutical content item indicates a number of prescriptions that a particular healthcare provider generates (e.g., writes) for a pharmaceutical article. In some implementations, the information source includes a prescription data source that indicates respective numbers of prescriptions that other healthcare providers in the same geographical region as the particular healthcare provider generated for the pharmaceutical article. In some implementations, the method 700 includes updating the first portion of the pharmaceutical content item to include the respective numbers of prescriptions that other healthcare providers generate for the pharmaceutical drug.

Figure 8:
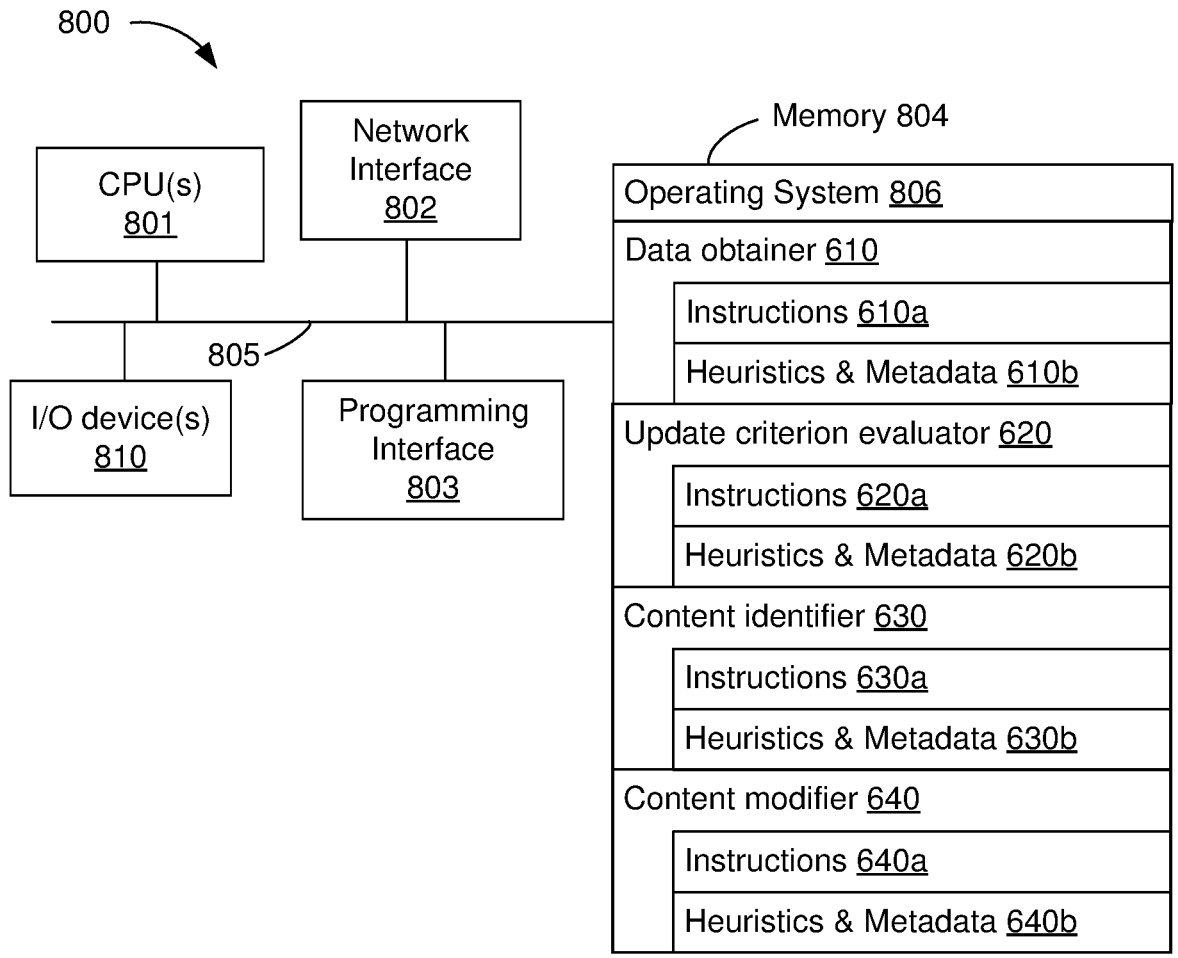
FIG. 8 is a block diagram of a device that updates a media content item in accordance with some implementations.

FIG. 8 is a block diagram of a device 800 that updates a media content item in accordance with some implementations. In some implementations, the device 800 implements the device 20 shown in FIGS. 1A-1E, the content presentation engine 200 shown in FIGS. 2 and 5A, the content updater 240 shown in FIGS. 2 and 5A-6, and/or the electronic device 60 shown in FIGS. 1D and 5A-5E. In some implementations, the device 800 is implemented by a server. In some implementations, the device 800 is implemented by a cloud computing platform. In some implementations, the device 800 is implemented by a portable electronic device (e.g., a smartphone, a tablet or a laptop). While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the device 800 includes one or more processing units (CPUs) 801, a network interface 802, a programming interface 803, a memory 804, one or more input/output (I/O) devices 810, and one or more communication buses 805 for interconnecting these and various other components.

In some implementations, the network interface 802 is provided to, among other uses, establish and maintain a metadata tunnel between a cloud hosted network management system and at least one private network including one or more compliant devices. In some implementations, the one or more communication buses 805 include circuitry that interconnects and controls communications between system components. The memory 804 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 804 optionally includes one or more storage devices remotely located from the one or more CPUs 801. The memory 804 comprises a non-transitory computer readable storage medium.

In some implementations, the memory 804 or the non-transitory computer readable storage medium of the memory 804 stores the following programs, modules and data structures, or a subset thereof including an optional operating system 806, the data obtainer 610, the update criterion evaluator 620, the content identifier 630 and the content modifier 640. In various implementations, the device 800 performs the method 700 shown in FIG. 7.

As described herein, in various implementations, the data obtainer 610 obtains (e.g., retrieves or receives) a request for a media content item (e.g., the request 510 shown in FIG. 6). To that end, the data obtainer 610 includes instructions 610a, and heuristics and metadata 610b.

As described herein, in various implementations, for each portion of the requested media content item, the update criterion evaluator 620 determines whether or not the portion satisfies an update criterion (e.g., the update criterion 242 shown in FIGS. 5A-6). To that end, the update criterion evaluator 620 includes instructions 620a, and heuristics and metadata 620b.

As described herein, in various implementations, for each portion of the requested media content item, the content identifier 630 utilizes a label associated with the portion to identify content that can be used to update the portion (e.g., the related content 632 shown in FIG. 6). To that end, the content identifier 630 includes instructions 630a, and heuristics and metadata 630b.

As described herein, in various implementations, in response to the update criterion evaluator 620 determining that a portion of the requested media content item satisfies an update criterion, the content modifier 640 modifies the portion of the requested media content item using the content identified by the content identifier 630. In some implementations, the content modifier 640 modifies the portion of the requested media content item by performing a combination of a write operation and a delete operation. To that end, the content modifier 640 includes instructions 640*a*, and heuristics and metadata 640*b*.

In various implementations, the one or more I/O devices 810 include one or more sensors. In some implementations, the one or more I/O devices 810 include an audio sensor (e.g., a microphone) for receiving an audible signal (e.g., an audible signal that corresponds to the request 510 shown in FIGS. 5A and 6). In some implementations, the one or more I/O devices 810 include a display for displaying information (e.g., for displaying the updated media content item 530 shown in FIG. 6). In some implementations, the one or more I/O devices 810 include a speaker for outputting an audible signal (e.g., an audible signal that corresponds to the updated media content item 530 shown in FIG. 6).

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
   at a device including a non-transitory memory and a processor coupled with the non-transitory memory:
      displaying a graphical user interface (GUI) for generating a new pharmaceutical content item, wherein the GUI includes a plurality of GUI elements including a name field for specifying a name of the new pharmaceutical content item and a label field for specifying a label associated with existing content that can be included in the new pharmaceutical content item;
      detecting, while the new pharmaceutical content item is being created, that the label field includes a first pharmaceutical label that is associated with a first portion of an existing pharmaceutical content item;
      in response to detecting that the label field includes the first pharmaceutical label, displaying an affordance that, when selected, triggers the device to include the first portion of the existing pharmaceutical content item into the new pharmaceutical content item; and
      in response to detecting a user selection of the affordance, including the first portion of the existing pharmaceutical content item into the new pharmaceutical content item that is being created.

2. The method of claim 1, wherein the existing pharmaceutical content item includes a document, an audio content item or a video content item.

3. The method of claim 1, wherein the existing pharmaceutical content item includes a plurality of pages, wherein the first pharmaceutical label is associated with a first subset of the plurality of pages, and wherein a second pharmaceutical label is associated with a second subset of the plurality of pages that is different from the first subset of the plurality of pages.

4. The method of claim 1, wherein the existing pharmaceutical content item includes a plurality of paragraphs, wherein the first pharmaceutical label is associated with a first subset of the plurality of paragraphs, and wherein a second pharmaceutical label is associated with a second subset of the plurality of paragraphs that is different from the first subset of the plurality of paragraphs.

5. The method of claim 1, wherein the existing pharmaceutical content item includes a video that spans a duration of time, wherein the first pharmaceutical label is associated with a first portion of the video that starts at a first time and ends at a second time, and wherein a second pharmaceutical label is associated with a second portion of the video that starts at a third time that is different from the first time and ends at a fourth time that is different from the second time.

6. A non-transitory memory storing one or more programs, which, when executed by one or more processors of a device, cause the device to:
   display a graphical user interface (GUI) for generating a new pharmaceutical content item, wherein the GUI includes a plurality of GUI elements including a name field for specifying a name of the new pharmaceutical content item and a label field for specifying a label associated with existing content that can be included in the new pharmaceutical content item;

detect, while the new pharmaceutical content item is being created, that the label field includes a first pharmaceutical label that is associated with a first portion of an existing pharmaceutical content item;

in response to detecting that the label field includes the first pharmaceutical label, display an affordance that, when selected, triggers the device to include the first portion of the existing pharmaceutical content item into the new pharmaceutical content item; and in response to detecting a user selection of the affordance, include the first portion of the existing pharmaceutical content item into the new pharmaceutical content item that is being created.

7. A device comprising:
one or more processors;
a non-transitory memory; and
one or more programs stored in the non-transitory memory, which, when executed by the one or more processors, cause the device to:
display a graphical user interface (GUI) for generating a new pharmaceutical content item, wherein the GUI includes a plurality of GUI elements including a name field for specifying a name of the new pharmaceutical content item and a label field for specifying a label associated with existing content that can be included in the new pharmaceutical content item;
detect, while the new pharmaceutical content item is being created, that the label field includes a first pharmaceutical label that is associated with a first portion of an existing pharmaceutical content item;
in response to detecting that the label field includes the first pharmaceutical label, display an affordance that, when selected, triggers the device to include the first portion of the existing pharmaceutical content item into the new pharmaceutical content item; and
in response to detecting a user selection of the affordance, include the first portion of the existing pharmaceutical content item into the new pharmaceutical content item that is being created.

8. The method of claim 1, wherein detecting that the label field includes the first pharmaceutical label that is associated with the first portion of the existing pharmaceutical content item comprises:
detecting text that was entered in the label field;
comparing the text with a plurality of pharmaceutical labels including the first pharmaceutical label; and
determining that the text matches the first pharmaceutical label.

9. The method of claim 1, wherein displaying the affordance comprises:
displaying a notification that includes:
the affordance for including the first portion of the existing pharmaceutical content item into the new pharmaceutical content item; and
another affordance that, when selected, triggers the device to not include the first portion of the existing pharmaceutical content item into the new pharmaceutical content item.

10. The method of claim 1, wherein including the first portion of the existing pharmaceutical content item into the new pharmaceutical content item comprises utilizing the first portion of the existing pharmaceutical content item as a template to populate at least a portion of the new pharmaceutical content item.

11. The method of claim 1, wherein the plurality of GUI elements further includes a content insertion field for inserting new content, and the method further comprises:

detecting text entered in the content insertion field;
determining that a portion of the text entered in the content insertion field matches a second pharmaceutical label that is associated with a second portion of the existing pharmaceutical content item; and
displaying a recommendation to include the second portion of the existing pharmaceutical content item into the new pharmaceutical content item.

12. The non-transitory memory of claim 6, wherein detecting that the label field includes the first pharmaceutical label that is associated with the first portion of the existing pharmaceutical content item comprises:
detecting text that was entered in the label field;
comparing the text with a plurality of pharmaceutical labels including the first pharmaceutical label; and
determining that the text matches the first pharmaceutical label.

13. The non-transitory memory of claim 6, wherein displaying the affordance comprises:
displaying a notification that includes:
the affordance for including the first portion of the existing pharmaceutical content item into the new pharmaceutical content item; and
another affordance that, when selected, triggers the device to not include the first portion of the existing pharmaceutical content item into the new pharmaceutical content item.

14. The non-transitory memory of claim 6, wherein including the first portion of the existing pharmaceutical content item into the new pharmaceutical content item comprises utilizing the first portion of the existing pharmaceutical content item as a template to populate at least a portion of the new pharmaceutical content item.

15. The non-transitory memory of claim 6, wherein the plurality of GUI elements further includes a content insertion field for inserting new content, and the method further comprises:
detecting text entered in the content insertion field;
determining that a portion of the text entered in the content insertion field matches a second pharmaceutical label that is associated with a second portion of the existing pharmaceutical content item; and
displaying a recommendation to include the second portion of the existing pharmaceutical content item into the new pharmaceutical content item.

16. The device of claim 7, wherein detecting that the label field includes the first pharmaceutical label that is associated with the first portion of the existing pharmaceutical content item comprises:
detecting text that was entered in the label field;
comparing the text with a plurality of pharmaceutical labels including the first pharmaceutical label; and
determining that the text matches the first pharmaceutical label.

17. The device of claim 7, wherein displaying the affordance comprises:
displaying a notification that includes:
the affordance for including the first portion of the existing pharmaceutical content item into the new pharmaceutical content item; and
another affordance that, when selected, triggers the device to not include the first portion of the existing pharmaceutical content item into the new pharmaceutical content item.

18. The device of claim 7, wherein including the first portion of the existing pharmaceutical content item into the new pharmaceutical content item comprises utilizing the first portion of the existing pharmaceutical content item as a template to populate at least a portion of the new pharmaceutical content item.

19. The device of claim 7, wherein the plurality of GUI elements further includes a content insertion field for inserting new content, and the method further comprises:
   detecting text entered in the content insertion field;
   determining that a portion of the text entered in the content insertion field matches a second pharmaceutical label that is associated with a second portion of the existing pharmaceutical content item; and
   displaying a recommendation to include the second portion of the existing pharmaceutical content item into the new pharmaceutical content item.

20. The device of claim 7, wherein the existing pharmaceutical content item includes a video that spans a duration of time, wherein the first pharmaceutical label is associated with a first portion of the video that starts at a first time and ends at a second time, and wherein a second pharmaceutical label is associated with a second portion of the video that starts at a third time that is different from the first time and ends at a fourth time that is different from the second time.

\* \* \* \* \*